(12) United States Patent
Duvold et al.

(10) Patent No.: US 6,593,319 B1
(45) Date of Patent: Jul. 15, 2003

(54) FUSIDIC ACID DERIVATIVES

(75) Inventors: Tore Duvold, Frederiksberg (DK); Welf von Daehne, Rungsted Kyst (DK)

(73) Assignee: Leo Pharmaceutical Products, Ltd. A/S, Ballerup (DK)

(*) Notice: Subject to any disclaimer, the term of this patent is extended or adjusted under 35 U.S.C. 154(b) by 0 days.

(21) Appl. No.: 09/787,539

(22) PCT Filed: Oct. 12, 2000

(86) PCT No.: PCT/DK00/00578
§ 371 (c)(1),
(2), (4) Date: Aug. 14, 2001

(87) PCT Pub. No.: WO01/29061
PCT Pub. Date: Apr. 26, 2001

(51) Int. Cl.[7] .................. A61K 31/70; A61K 31/58; A61K 31/56; C07C 221/22; C07C 13/00; C07C 31/00; C07C 9/00
(52) U.S. Cl. .................. 514/178; 552/523; 552/525; 552/530; 552/540; 546/77; 514/23; 514/25; 514/172; 514/182; 536/18.6
(58) Field of Search .................. 552/523, 525, 552/540, 530; 514/25, 23, 172, 178, 182; 536/18.6, 5, 4.1; 546/77

(56) References Cited

U.S. PATENT DOCUMENTS

| | | | |
|---|---|---|---|
| 4,162,259 A | 7/1979 | von Daehne et al. .... | 260/397.1 |
| 4,259,333 A | 3/1981 | Binderup .................... | 424/246 |
| 4,548,922 A | * 10/1985 | Carey et al. ................... | 514/4 |
| 4,959,358 A | * 9/1990 | Carey et al. ................ | 514/171 |
| 6,103,884 A | 8/2000 | Koreeda et al. ............... | 536/5 |

FOREIGN PATENT DOCUMENTS

| | | |
|---|---|---|
| EP | 0 020 794 | 1/1983 |
| EP | 0 408 330 A2 | 1/1991 |
| GB | 1 316 556 | 5/1973 |
| GB | 2 013 084 | 8/1979 |
| WO | WO 86/03966 | 7/1986 |

OTHER PUBLICATIONS

Prehn et al. (DN 68:75913, HCAPLUS, abstract of Acta Pathol. Microbiol. Scand. (1967), 71(1), 135–140).*

Bendtzen, Klaus (DN 114:157194, HCAPLUS, abstract of WO9004398).*

* cited by examiner

Primary Examiner—Sabiha Qazi
(74) Attorney, Agent, or Firm—Birch, Stewart, Kolasch & Birch, LLP

(57) ABSTRACT

Novel 17,20-dihydrofusidic acid derivatives are used in pharmaceutical compositions for the treatment of infections, in particular in topical compositions for the treatment of skin or eye infections.

19 Claims, No Drawings

FUSIDIC ACID DERIVATIVES

This application is the national phase of PCT International Application No. PCT/DK00/00598 filed on Oct. 12, 2000 under 35 U.S.C. §371. The entire contents of the above-identified application is hereby incorporated by reference. This application also claims priority of Application No. 60/159,557 filed in the United States on Oct. 15, 1999 under 35 U.S.C. §120.

FIELD OF THE INVENTION

The present invention relates to a novel series of 17,20-dihydrofusidic acid derivatives, to salts and to easily hydrolysable esters thereof, to the preparation of these compounds, to pharmaceutical compositions containing the compounds and to the use of such compounds in medicine. In particular, these compounds exhibit antimicrobial activity, thus they are useful for the treatment of infectious diseases. The compounds of the present invention can be used both in systemic treatment of infections and in topical treatment of infections related to skin and eyes.

BACKGROUND OF THE INVENTION

The antibacterial properties of fusidic acid are well known. It is also known that structural variations may cause significant or total loss of such activity (cf. Godtfredsen et al, *J. Med. Chem.*, Vol. 9, p. 15–22, 1966). It has until now been generally accepted that the double bond between the carbon atoms C-17 and C-20 which connect the side-chain to the tetracyclic ring system was essential for any antibacterial activity. Reduction of the double bond between C-24 and C-25 of fusidic acid to a single bond resulted in a marginal effect on the antibacterial activity of the molecule whereas additional reduction of the double bond between C-17 and C-20 yielding tetrahydrofusidic acid caused almost complete loss of activity. Two epimers in the series of tetrahydrofusidic acids have earlier been prepared by means of catalytic hydrogenation of fusidic acid or its isomer lumi-fusidic acid, having the configuration 17(R),20(S) and 17(R),20(R) respectively (cf. von Daehne et al., *Adv. Appl. Microbiol.*, 25, p. 95–146, 1979, and references cited therein).

SUMMARY OF THE INVENTION

The purpose of the invention is to provide semisynthetic analogues of fusidic acid having antimicrobial activity. Said purpose is achieved with the compounds of the present invention belonging to the series of dihydro- and tetrahydrofusidic acids having the essential configuration 17(S),20(S) which in vitro show high antimicrobial activity and favourable stability and pharmacokinetic properties, whereby the compounds of the invention may be used in treatment of infections in humans and animals.

The present invention provides compounds of the general formula Ia:

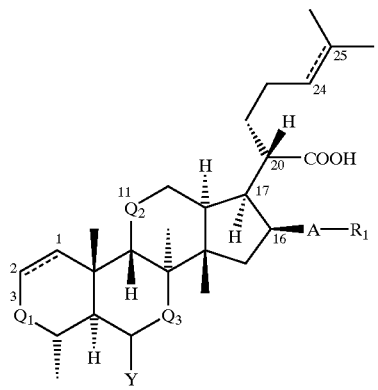

wherein
$Q_1$, $Q_2$ and $Q_3$ are the same or different and independently represent a —(CO)— group; a —(CHOH)— group; a —(CHOR)— group; a —(CHSH)— group; a —(NH)— group; a —(CHNH$_2$)— group; or a —(CHNHR)— group, wherein R represents an alkyl radical having 1 to 4 carbon atoms or an acyl radical having 1 to 4 carbon atoms; and wherein $Q_2$ and $Q_3$ may also independently represent a —(CH$_2$)— group;

Y represents hydrogen, hydroxy, an alkyl radical having 1 to 4 carbon atoms, or an acyl radical having 1 to 4 carbon atoms; A represents an oxygen or a sulphur atom;

$R_1$ represents an alkyl radical having 1 to 4 carbon atoms, an olefinic group having 2 to 4 carbon atoms, a ($C_1$–$C_6$) acyl group, ($C_3$–$C_7$)cycloalkylcarbonyl group or a benzoyl group, $R_1$ optionally being substituted with one or more halogen atoms and/or hydroxy, alkoxy or azido groups;

and pharmaceutically acceptable salts and easily hydrolysable esters thereof.

In formula Ia and subsequent formulas herein the dotted lines between C-1 and C-2 and/or C-24 and C-25 indicate that the atoms in question are connected with either a double bond or a single bond.

DETAILED DESCRIPTION OF THE INVENTION

Preferred compounds of the invention are compounds of formula I

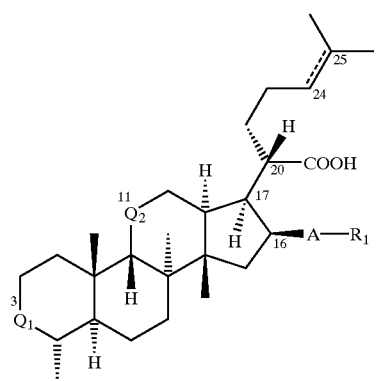

wherein
$Q_1$ and $Q_2$ are the same or different and both represent a —(CHOH)— group; a —(CO)— group; or a —(CHSH)— group;

A represents an oxygen or a sulphur atom;

R$_1$ represents an alkyl radical having 1 to 4 carbon atoms, an olefinic group having 2 to 4 carbon atoms, a (C$_1$–C$_6$) acyl group, (C$_1$–C$_7$)cycloalkylcarbonyl group or a benzoyl group, R$_1$ optionally being substituted with one or more halogen atoms and/or hydroxy, alkoxy or azido groups; and pharmaceutically acceptable salts and easily hydrolysable esters thereof.

Preferably Q$_1$ and Q$_2$ are selected from the group consisting of —(CO)— and —(CHOH)—. More preferred compounds of the invention are compounds of formula I wherein Q$_1$ and Q$_2$ both represent a

group or one of Q$_1$ or Q$_2$ represents —(CO)—; A represents oxygen; R$_1$ represents a (C$_1$–C$_4$)alkyl group, optionally substituted with one or more substituents selected from the group consisting of azido, hydroxy, and halogen selected from fluoro, chloro and bromo, or R$_1$ represents an acyl group with 1 to 4 carbon atoms or a benzoyl group, both optionally substituted with one or more halogen atoms, preferably selected from the group consisting of fluoro and chloro. R$_1$ is preferably selected from the group consisting of ethyl, 2,2,2-trifluoroethyl, 2,2,2-trichloroethyl, 2-azidoethyl, 2-hydroxyethyl, propyl and isopropyl, 1,3-difluoro-isopropyl, acetyl, propionyl, chloroacetyl and trifluoroacetyl, or R$_1$ is selected from the preferred group consisting of ethyl, 2,2,2-trichloroethyl, 2-azidoethyl, isopropyl, tert-butyl and acetyl. Also preferred are compounds of formula I and Ia wherein the bond between C-24 and C-25 is a double bond.

Examples of compounds of the invention which can all be prepared by the methods described below are:
17(S),20(S)-Dihydrofusidic acid,
17(S),20(S),24,25-Tetrahydrofusidic acid,
11-Dehydro-17(S),20(S)-dihydrofusidic acid,
3-Dehydro-17(S),20(S)-dihydrofusidic acid,
16-Deacetoxy-16β-propionyloxy-17(S),20(S)-dihydrofusidic acid,
16-Deacetoxy-16β-(3'-chloropropionyloxy)-17(S),20(S)-dihydrofusidic acid,
16-Deacetoxy-16β-(2'-methylpropionyloxy)-17(S),20(S)-dihydrofusidic acid,
16-Deacetoxy-16β-cyclopropylcarbonyloxy-17(S),20(S)-dihydrofusidic acid,
16-Deacetoxy-16β-chloroacetoxy-17(S),20(S)-dihydrofusidic acid,
16-Deacetoxy-16β-bromoacetoxy-17(S),20(S)-dihydrofusidic acid,
16-Deacetoxy-16β-benzoyloxy-17(S),20(S)-dihydrofusidic acid,
16-Deacetoxy-16β-(4'-fluorobenzoyloxy)-17(S),20(S)-dihydrofusidic acid,
16-Deacetoxy-16β-cyclohexylcarbonyloxy-17(S),20(S)-dihydrofusidic acid,
16-Deacetoxy-16β-acryloyloxy-17(S),20(S)-dihydrofusidic acid,
16-Deacetoxy-16β-isopropylthio-17(S),20(S)-dihydrofusidic acid,
16-Deacetoxy-16β-ethylthio-17(S),20(S)-dihydrofusidic acid,
16-Deacetoxy-16β-(2',2',2'-trichloroethylthio)-17(S),20(S)-dihydrofusidic acid,
16-Deacetoxy-16β-tert-butylthio-17(S),20(S)-dihydrofusidic acid,
16-Deacetoxy-16β-methoxymethylthio-17(S),20(S)-dihydrofusidic acid,
16-Deacetoxy-16β-isopropylthio-17(S),20(S);24,25-tetrahydrofusidic acid,
16-Deacetoxy-16β-acetylthio-17(S),20(S)-dihydrofusidic acid,
16-Deacetoxy-16β-benzoylthio-17(S),20(S)-dihydrofusidic acid,
16-Deacetoxy-16β-ethoxy-17(S),20(S)-dihydrofusidic acid,
16-Deacetoxy-16β-(2',2',2'-trifluoroethoxy)-17(S),20(S)-dihydrofusidic acid,
16-Deacetoxy-16β-propoxy-17(S),20(S)-dihydrofusidic acid,
16-Deacetoxy-16β-isopropoxy-17(S),20(S)-dihydrofusidic acid,
16-Deacetoxy-16β-(1',3'-difluoroisopropoxy)-17(S),20(S)-dihydrofusidic acid,
16-Deacetoxy-16β-methoxymethoxy-17(S),20(S)-dihydrofusidic acid,
16-Deacetoxy-16β-(2',2',2'-trichloroethoxy)-17(S),20(S)-dihydrofusidic acid,
16-Deacetoxy-16β-(2'-azidoethoxy)-17(S),20(S)-dihydrofusidic acid,
16-Deacetoxy-16β-(2'-hydroxyethoxy)-17(S),20(S)-dihydrofusidic acid,
and pharmaceutically acceptable salts and easily hydrolysable esters thereof.

In contrast to natural fusidic acid (1) wherein C-17 and C-20 are connected with a double bond, all compounds described herein and by formula I and Ia have a single bond between C-17 and C-20. The configuration of the two asymmetric carbon atoms in question is 17(S) and 20(S). This epimer is one of four possible epimers differing solely in the configuration of C-17 and C-20, and biological tests have shown this to be the only epimer exhibiting potent activity.

The compounds of the invention can be used as such or in the form of salts or easily hydrolysable esters (as hereinafter defined). The salts of the compounds are especially the pharmaceutically acceptable salts, such as alkali metal salts and alkaline earth metal salts, for example sodium, potassium, magnesium or calcium salts, as well as silver salts and salts with bases, such as ammonia or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine. The silver salts of the compounds are especially useful for local treatment.

The expression "easily hydrolysable esters" is used in this specification to denote alkanoyloxyalkyl, aralkanoyloxyalkyl, aroyloxyalkyl, for example acetoxymethyl, pivaloyloxymethyl, benzoyloxymethyl esters and the corresponding 1'-oxyethyl derivatives, or alkoxycarbonyloxyalkyl esters, for example methoxycarbonyloxymethyl esters and ethoxycarbonyloxymethyl esters, and the corresponding 1'-oxyethyl derivatives, or lactonyl esters, for example phthalidyl esters, or dialkylaminoalkyl esters, for example diethylaminoethyl esters. The expression "easily hydrolysable esters" includes in vivo hydrolysable esters of the compounds of the invention. Such esters may be prepared using methods known to a skilled person in the art, cf. GB patent No. 1 490 852 hereby incorporated by reference.

As used in the specification, unless specified to the contrary, the following terms have the meanings indicated, cf. also IUPAC Recommendations 1994 http://www.chem.qmw.ac.uk/iupac/class/.

"Alkyl" refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, including for example (C$_1$–C$_4$)alkyl, (C$_1$–C$_3$)

alkyl, ($C_1$–$C_2$)alkyl, methyl, ethyl, n-propyl, isopropyl, n-butyl, isobutyl, sec-butyl, and t-butyl. Alkane refers to an acyclic branched or unbranched hydrocarbon having the general formula $C_nH_{2n+2}$, where n represents an integer, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, ($C_2$–$C_4$)olefinic group, preferably a ($C_2$–$C_4$)alkenyl; ($C_2$–$C_3$)olefinic group, preferably a ($C_2$–$C_3$)alkenyl; vinyl; allyl; 1-butenyl; 2-butenyl; and 2-methyl-2-propenyl. Further, "olefinic group" refers to a straight or branched alkynyl moiety having at least one triple bond. This term would include, for example, crotyl and propargyl. Olefinic groups having only one carbon-carbon double bond, herein called alkenyl, are preferred.

"Aryl" refers to groups derived from monocyclic and polycyclic aromatic hydrocarbons by removal of a hydrogen atom from a ring carbon atom, e.g. o-tolyl, phenyl, naphthyl. The number of carbon atom in an aryl group is typically 6, 7, 8, 9 or 10.

"Acyl" refers broadly to a radical of the formula R—CO—, where R is alkyl as defined above, for example ($C_1$–$C_6$)acyl.

"Alkoxy" refers broadly to a radical of the formula —OR, where R is alkyl as defined above, for example ($C_1$–$C_5$) alkoxy, ($C_1$–$C_3$)alkoxy, methoxy, n-propoxy, t-butoxy, and the like.

"Halogen" means the same or different of fluoro, chloro, bromo, and iodo; fluoro, chloro, and bromo being more useful in the present compounds.

"Alkanoyl" refers broadly to a radical of the formula —R—CO—, where R is alkyl as defined above, for example ($C_1$–$C_8$)alkanoyl, acetyl, propionyl, isopropionyl, butyryl. "Aralkanoyl" refers broadly to a radical of the formula —R($CH_2$)$_n$—CO—, wherein R is aryl as defined above and n is an integer, preferably selected from 1, 2, 3, and 4. "Aroyl" refers broadly to R—CO— where R is an aryl group as defined above.

"Alkanoyloxyalkyl" or "aroyloxyalkyl" refer broadly to a radical of the formula —$CH_2$—O—CO—R, wherein R represents a ($C_1$–$C_6$)alkyl group or a ($C_6$–$C_8$)aryl group. Aryl and alkyl are as defined above.

"Alkoxycarbonyl-" and "aryloxycarbonyl-" refer to the group —CO—OR or "acyloxy-" refers to the group R—CO—O— wherein R is alkyl or aryl as defined above.

There are several chiral centres in the compounds according to the invention because of the presence of asymmetric carbon atoms. The presence of several asymmetric carbon atoms gives rise to a number of stereoisomers with R or S configuration at each chiral centre. General formula I and Ia, and (unless specified otherwise) all other formulae in this specification are to be understood to include all such stereoisomers in pure form and as mixtures (for example stereoisomeric mixtures) except where the configuration is expressly indicated.

In the compounds of formula I and Ia, the preferred stereochemistry is in general as follows: when $Q_1$ and $Q_2$ refer to the

group the configuration at C-3 and C-11 in the compounds of formula I and Ia is 3α and 11α, respectively. The C-16 atom carrying the A group has the (S)-configuration, hereinafter denoted 16β. In the formulas herein plain lines depict bonds approximately in the plane of the drawing; bonds to atoms above the plane are shown with a bold wedge starting from an atom in the plane of the drawing at the narrow end of the wedge; and bonds to atoms below the plane are shown with short parallel (wedged) lines. Substituents above the plane are described as β and shown as a bold wedge, those below the plane are described as α and shown by a line with short parallel (wedged) lines.

Biological Activity

In vitro investigations have evidenced high potency of compounds of the invention against several bacteria including staphylococci, streptococci, corynebacteriae and mycobacteriae. Biological tests have revealed comparable antibacterial activity of 17(S),20(S)-dihydrofusidic acid (10) (Compound 101) to that of fusidic acid (1) as can be seen from Table 1 showing MIC values of the two mentioned compounds towards a number of bacteria. The biological tests are conducted on microtitter plates using liquid medium containing broth.

TABLE 1

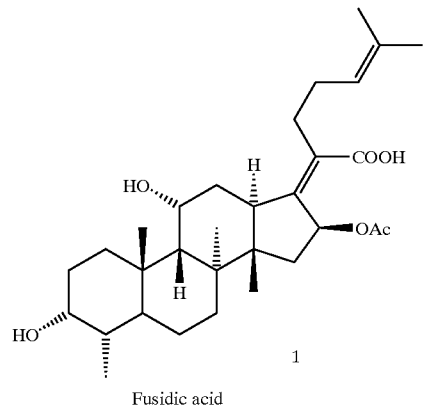

Fusidic acid

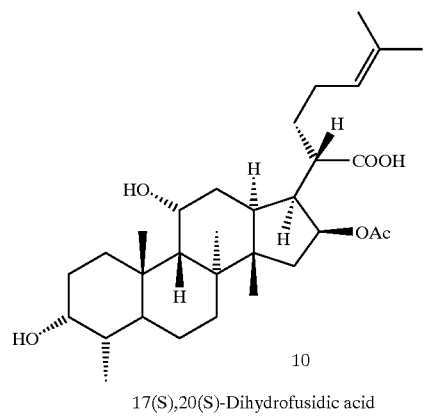

17(S),20(S)-Dihydrofusidic acid

| Name of bacteria/strain | Comment | MIC values (concentrations in µg/ml) required for 90% inhibition) | |
|---|---|---|---|
| | | Compound 101 | Fusidic acid (1) |
| S. aureus/1 Aus-pe | FusS, MRSA | 1 | 1 |
| S. aureus/ATCC 29213 | FusS, MSSA | 1 | 1 |
| S. aureus/22 DK | FusS, MSSA | 1 | 0.5 |
| S. aureus/54 USA-br | FusR, MSSA | 8 | 8 |
| E. faecalis/ V583 P. Cour. | VanR | 16 | 16 |
| C. diphteria/62001 | | 0.063 | 0.063 |
| Streptococcus - gr.A/67011 | | 64 | 16 |
| Streptococcus - gr.B/61 | | >64 | 32 |
| Streptococcus - gr.C/68 | | 4 | 2 |

TABLE 1-continued

| | | | |
|---|---|---|---|
| Streptococcus - gr.G/59 | | 8 | 4 |
| Staphylococcus/291-2* | FusS | 1 | 1 |
| Staphylococcus/379-2* | FusR | 64 | 64 |
| P. acnes/1060 | | 0.5 | 0.125 |
| N. gonorrhoea/C1 | | 4 | 1 |
| N. meningitidis/K1 | | 1 | 0.25 |
| M. tuberculosis/R 498 | | 16 | >16 |

FusS = fusidic acid sensitive;
FusR = fusidic acid resistant;
MRSA = methicillin resistant *Staphyloccus aureus*;
MSSA = methicillin sensitive *Staphyloccus aureus*;
VanR = Vancomycin resistant.*
Coagulase negative.

Also other compounds of the invention exhibit high in vitro activity against several bacteria. The antibacterial activity of some of these compounds relative to fusidic acid appears from Table 2 showing MIC values for compounds of the invention. The method used is recommended by the European Pharmacopoeia 3rd Ed. (1997) for testing the potency of antibiotics. It is an agar diffusion method where the same volume of the tested solution is added to cavities in agar. The inhibition zones are a function of the concentration of the fusidic acid analogue used. All assays are run with fusidic acid (1) as the reference substance. The results in Table 2 differ from those of Table 1 due to the different experimental methods used.

TABLE 2

| | MIC values (concentrations in μg/ml required for 90% inhibition) | | | | | | |
|---|---|---|---|---|---|---|---|
| Strain | Fusidic acid (1) | 101 | 102 | 105 | 113 | 123 | 128 |
| S. aureus ATCC6538P | 0.013 | 0.002 | 0.016 | 0.22 | 16 | 0.02 | 0.26 |
| S. aureus* Leo id. CJ232 | 0.012 | 0.003 | 0.12 | 0.24 | 16 | 0.005 | >64 |
| S. aureus** Leoid CJ234(R) | 0.01 | 0.001 | 0.009 | 0.063 | 16 | 0.007 | >64 |
| S. aureus ATCC2977 | 0.01 | 0.001 | 0.02 | 0.19 | 16 | 0.02 | 0.19 |
| Strep. epidermis A. ATCC12228 | 0.01 | 0.001 | 0.015 | 0.08 | >64 | 0.5 | 0.5 |
| Strep. faecalis ATCC10541 | 4.9 | 3.7 | MIC>64 | >64 | >64 | 16 | 16 |
| Strep. faecium*** Leo id. E119(P) | 2.7 | 1.2 | 3.9 | 3.9 | >64 | 16 | 16 |
| Strep. sp. Gr.B Leo id. EF6 | 4.9 | 3.5 | 3.4 | >64 | 4 | 16 | 16 |

*MRSA
**MRSA and Rifampicin resistant
***Penicillin resistant

Furthermore, compounds of the invention possess several advantages compared to the corresponding compounds containing the 17,20 double bond, such as fusidic acid:

The compounds of formula I and Ia are chemically more stable, possibly due to the lower acidity of the saturated 17,20 bond and the absence of conjugation of the carboxylic acid with a carbon-carbon double bond.

The compounds of formula I and Ia are less easily degraded when exposed to sunlight.

The compounds of formula I and Ia are more stable in solution: A solution of the compound of formula 10 shown below in ethanol stored at 0° C. for 1 month retained >80% of initial activity whereas a corresponding solution of fusidic acid retained only about 70% of initial activity.

The compounds of formula I and Ia are more lipophilic and thus more suitable for topical preparations.

Being semi-synthetic the compounds of formula I may be prepared from a relatively crude fusidic acid raw material which is otherwise not suitable for medicinal purposes.

The following standard abbreviations are used throughout this disclosure:

AcOH=acetic acid
$Ac_2O$=acetic anhydride
Ac=acetyl
Bu=n-butyl
'Bu, tBu=tert-butyl
Et=ethyl
Ether=diethyl ether
Me=methyl
MOM=methoxymethyl
MOMO=methoxymethyl-O
Ph=phenyl
TBAF=tetra-n-butylammonium fluoride
TBS=tert.butyl dimethylsilyl
TBSCl=tert.butyl dimethylsilyl chloride
THF=tetrahydrofuran
TLC=Thin Layer Chromatography
TMS=trimethylsilyl Preparations of Compounds of the Invention 17S,20S-Dihydrofusidic acid (10) may be prepared starting from naturally occurring fusidic acid by the sequence outlined in Scheme 1 below: Fusidic acid (1) is first converted into lactone (2) by deacetylation followed by acidification. The double bond between C-17 and C-20 in (2) is reduced with $NaBH_4$ in aqueous methanol with cis attack from the α-face of the molecule yielding lactone (3). Inversion at C-20 is obtained quantitatively by heating lactone (3) in the presence of 28% aqueous sodium hydroxide. The hydroxy groups at C-3 and C-11 in lactone (4) are subsequently protected as methoxymethyl (MOM) ethers. Reduction of the protected lactone (5) with $LiAlH_4$ yields diol (6) which is first protected selectively at the primary hydroxy group at C-21 with a diphenylmethylsilyl group followed by acetylation of the hydroxy group at C-16. After desilylation of (7) using tetrabutylammonium fluoride (TBA⁺F⁻) buffered with acetic acid, the free hydroxy group in (8) can be oxidised, first to the aldehyde by Dess-Martin periodinane and further to the carboxylic acid (9) by sodium chlorite. Compound (10) is obtained in a final step by cleavage of the MOM groups in (9) by treating with trimethylsilyl bromide (TMSBr) in anhydrous dichloromethane.

The compound of formula 10 is a compound of the invention (Compound 101) and further a general starting compound for analogues corresponding to formula I as hereinafter described.

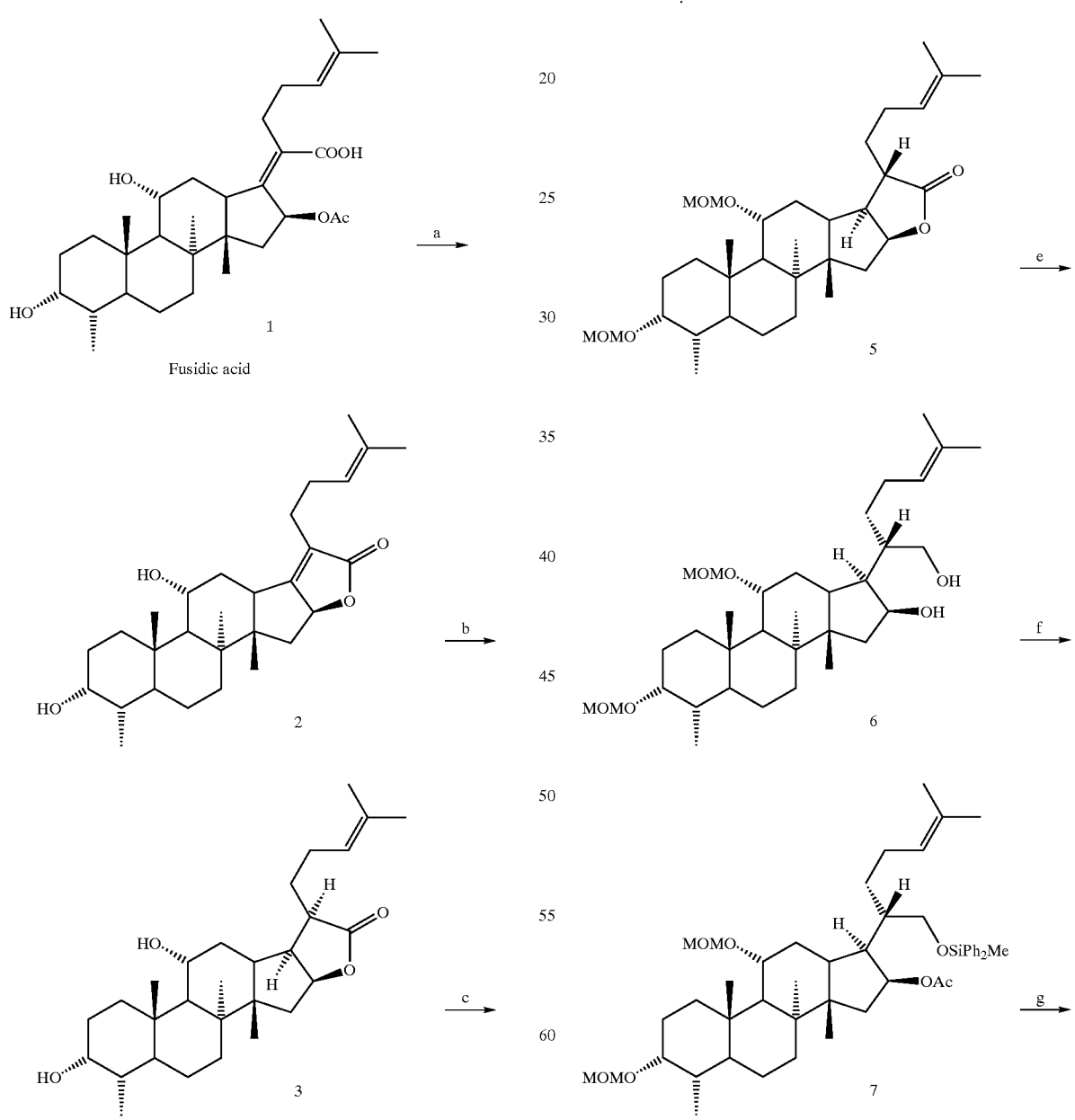

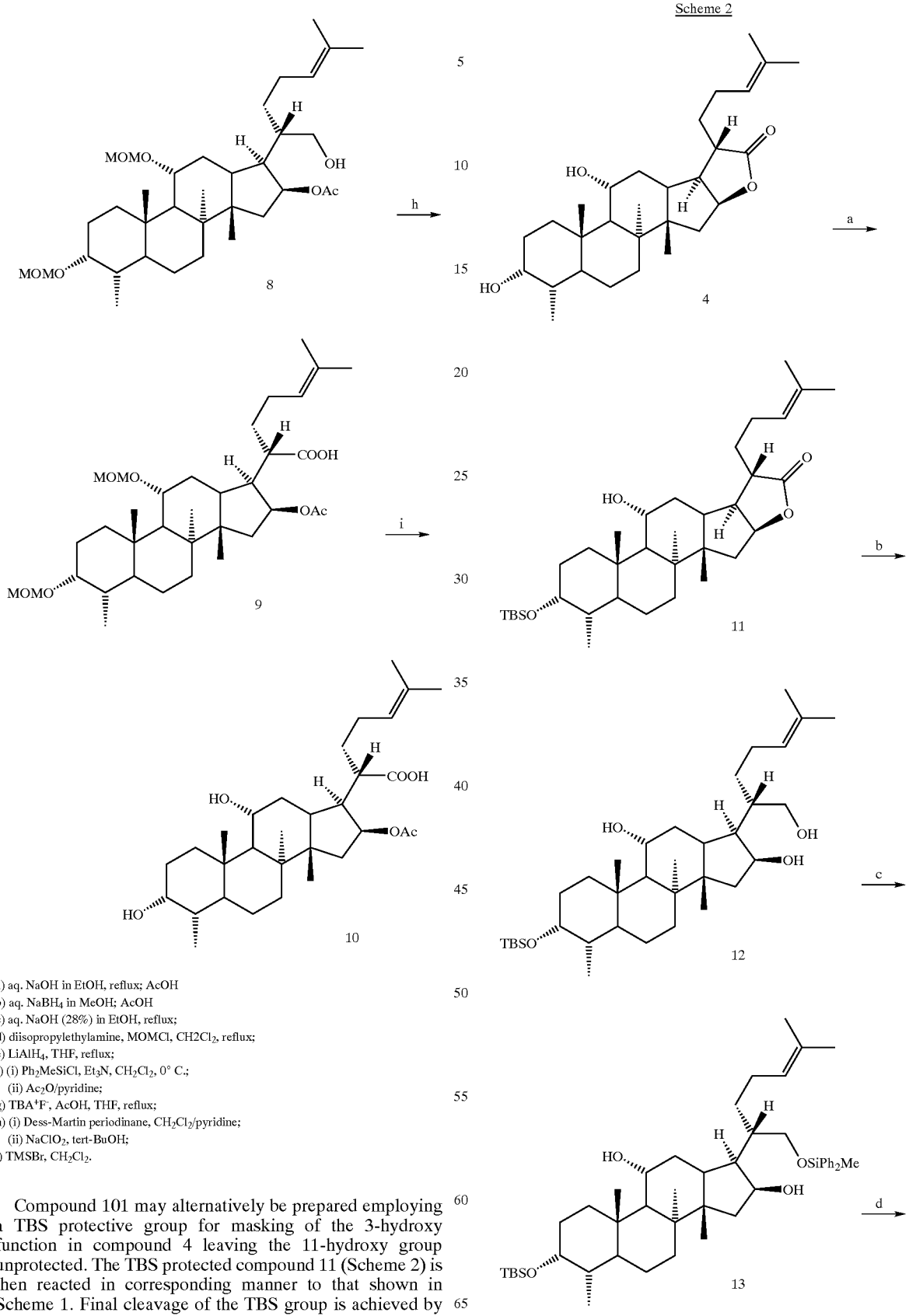

a) aq. NaOH in EtOH, reflux; AcOH
b) aq. NaBH$_4$ in MeOH; AcOH
c) aq. NaOH (28%) in EtOH, reflux;
d) diisopropylethylamine, MOMCl, CH2Cl$_2$, reflux;
e) LiAlH$_4$, THF, reflux;
f) (i) Ph$_2$MeSiCl, Et$_3$N, CH$_2$Cl$_2$, 0° C.;
   (ii) Ac$_2$O/pyridine;
g) TBA$^+$F$^-$, AcOH, THF, reflux;
h) (i) Dess-Martin periodinane, CH$_2$Cl$_2$/pyridine;
   (ii) NaClO$_2$, tert-BuOH;
i) TMSBr, CH$_2$Cl$_2$.

Compound 101 may alternatively be prepared employing a TBS protective group for masking of the 3-hydroxy function in compound 4 leaving the 11-hydroxy group unprotected. The TBS protected compound 11 (Scheme 2) is then reacted in corresponding manner to that shown in Scheme 1. Final cleavage of the TBS group is achieved by treating compound 16 with diluted hydrofluoric acid yielding the compound of formula 10 (Compound 101).

13

-continued

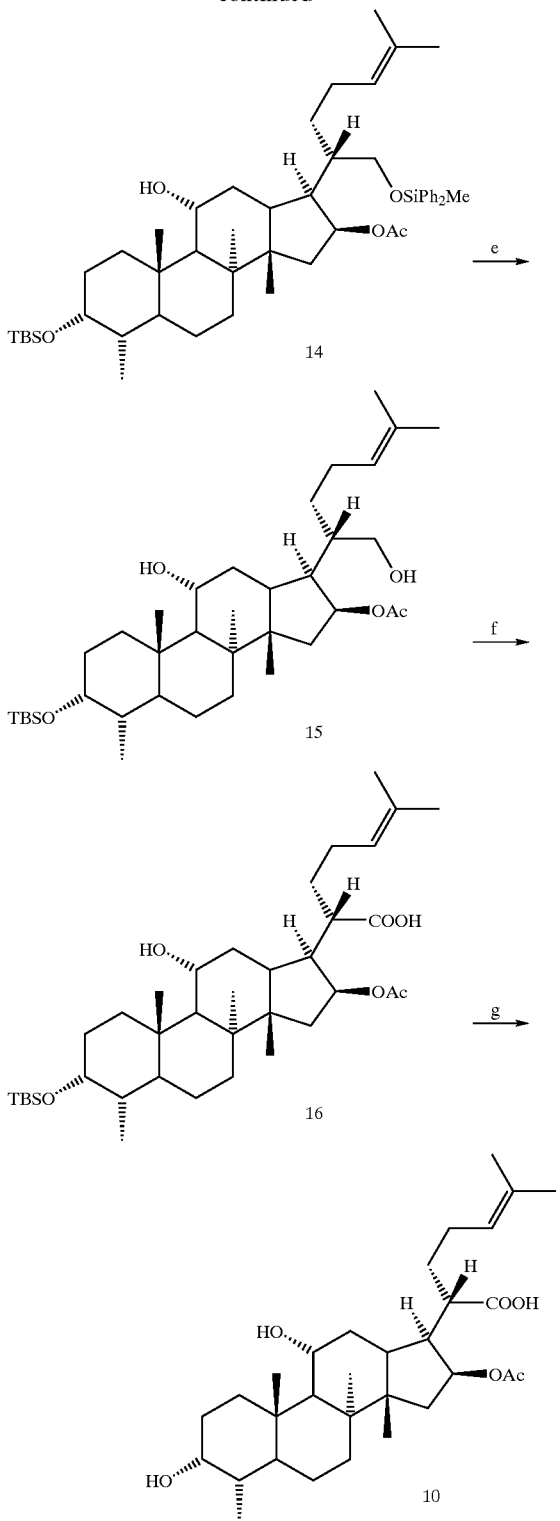

a) imidazol, TBSCl, CH$_2$Cl$_2$;
b) LiAlH$_4$, THF, reflux;
c) Ph$_2$MeSiCl, Et$_3$N, CH$_2$Cl$_2$, 0° C.;
d) Ac$_2$O/pyridine;
e) TBA$^+$F$^-$, AcOH, THF, reflux;
f) (i) Dess-Martin periodinane, CH$_2$Cl$_2$/pyridine;
   (ii) NaClO$_2$, tert-BuOH;
g) aq. HF, acetonitrile/THF.

14

The compounds of general formula I may be prepared by a method comprising a first step in which compounds of the general formula II is converted into 16-bromo compounds of formula III as described below.

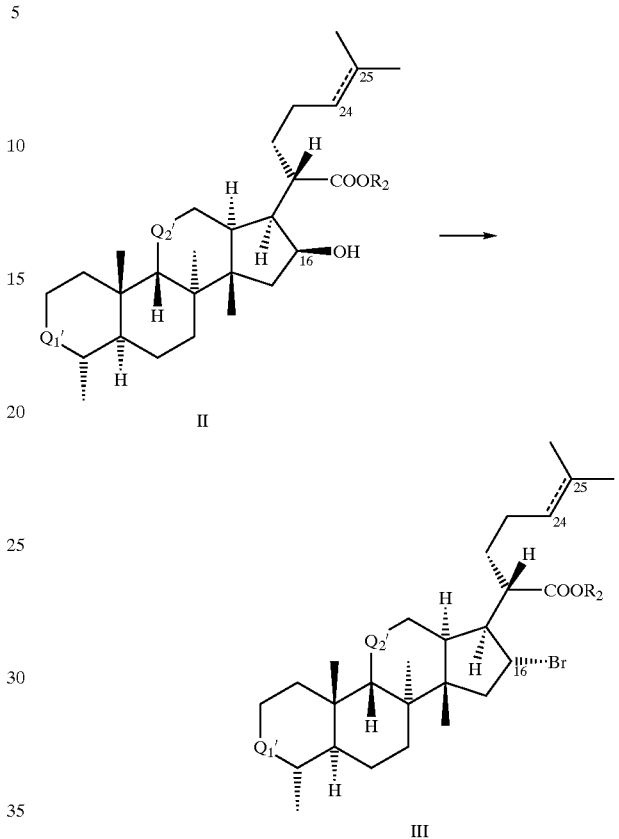

in which formulas $Q_1'$ and $Q_2'$ represent a —(CO)— group, a $\overset{H}{\underset{HO^{\prime\prime\prime\prime}}{\diagdown}}$ group, or a $\overset{H}{\underset{R_3O^{\prime\prime\prime\prime}}{\diagdown}}$ group, $R_3$ representing a common protective group such as alkanoyl, aralkanoyl, alkanoyloxyalkyl or aroyl, or a trisubstituted silyl radical substituted with alkyl, oxyalkyl, aryl or oxyaryl groups; $R_2$ is a straight or a branched alkyl radical having from 1–6 carbon atoms, e.g. methyl, ethyl, tert-butyl, an unsubstituted or substituted aralkyl radical, e.g. benzyl, nitrobenzyl, an alkanoylmethyl or aroylmethyl radical, e.g. acetonyl or phenacyl, an alkanoyloxyalkyl, or aroyloxyalkyl radical, e.g. acetoxymethyl, pivaloyloxymethyl or benzoyloxymethyl, an alkoxymethyl radical or a cyanomethyl radical, a silyl radical substituted with groups of alkyl, alkenyl, oxyalkyl, oxyalkenyl, aryl or oxyaryl, e.g. triethylsilyl, triisopropylsilyl, diphenylmethylsilyl, tert-butyldimethylsilyl, tert-butyldiphenylsilyl, tert-butoxydiphenylsilyl; the dotted line between C-24 and C-25 has the meaning as defined above.

The conversion is performed by reacting a compound of formula II with tetrabromomethane/triphenylphosphine or with N,N-dimethylformimidate bromide in an inert solvent, e.g. ether, tetrahydrofuran or dimethylformamide, and at or below room temperature (cf. von Daehne, W. and Rasmussen, P., 1975, GB Patent No. 1 523 803).

Compounds of formula II are prepared starting from compounds in Scheme 1 by methods known from the literature (cf. GB Patent No. 1 490 852 and GB Patent No. 1 523 803) or by analogous methods. Starting compounds of formula III can for instance be prepared from the compound of formula 10 or more conveniently from the compound of formula 9 as outlined in Scheme 3.

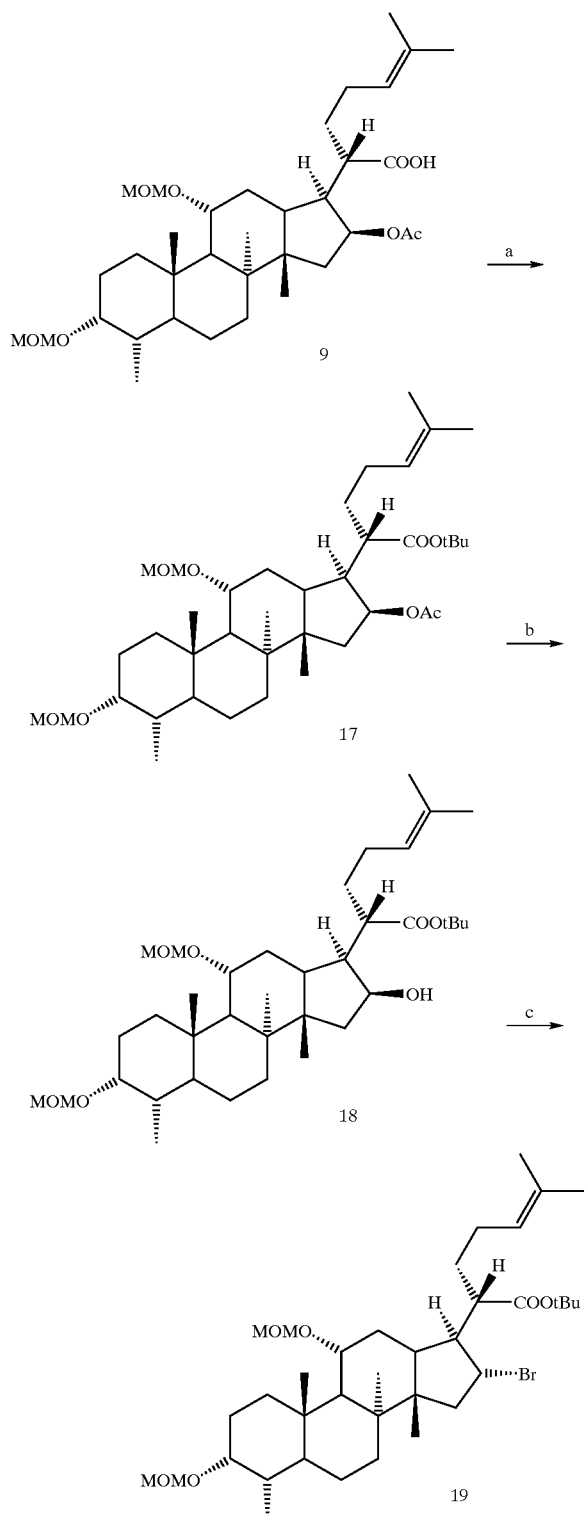

a) N,N-Dimethylformamide-bis-tert-butyl acetate, benzene, reflux;
b) 2N aqueous NaOH, EtOH; reflux
c) CBr$_4$, PPh$_3$, CH$_2$Cl$_2$.

In a next step intermediates of formula III are reacted with compounds of formula IV to form, with inversion of configuration at C-16, compounds of formula V:

in which formulae $Q_1'$, $Q_2'$, A, $R_1$, $R_2$ and the dotted line between C-24 and C-25 have the meanings defined above. The conversions are performed according to procedures known from the literature (cf. von Daehne, W. and Rasmussen, P., 1975, GB Patent No. 1 523 803). When A in formula V represents oxygen and $R_1$ is different from acyl, the reacting compounds of formula IV are preferably used as solvents and the reaction is performed in the presence of a silver or mercury salt, e.g. silver carbonate, silver trifluoroacetate or mercury acetate, or a base, e.g. potassium carbonate, sodium bicarbonate or sodium ($C_1$–$C_5$) alcoholate, preferably sodium methanolate or sodium ethanolate, and at room temperature or slightly elevated temperature. If A in formula V represents sulphur and $R_1$ is different from acyl, the reaction is performed in an inert organic solvent, preferably ethanol or dimethylformamide, in the presence of a base, e.g. potassium hydroxide or sodium hydride, and at or below room temperature or slightly elevated temperature.

When A in formula V represents oxygen and $R_1$ represents acyl, the reaction is carried out with the corresponding silver salts of the compounds of formula IV in an inert solvent, e.g. benzene, and at room temperature or slightly elevated temperature. When A in formula V represents sulphur and $R_1$ represents acyl, the reacting compounds of formula IV are preferably used as their potassium or sodium salts and the reaction is performed in an inert solvent, e.g. dimethylformamide, and at room temperature.

The compounds of formula V, wherein A represents oxygen and $R_1$ represents a ($C_1$–$C_6$)acyl group or a benzoyl group, can be prepared from the compounds of formula II by reaction with a reactive derivative of the carboxylic acids of formula IV, e.g. an acid chloride or acid anhydride. The reaction is performed in the presence of a base, preferably pyridine, in an inert solvent, e.g. dimethylformamide or pyridine, and at or below room temperature.

In a final step the compounds of formula V can be converted into the compounds of formula I by hydrolysis, either in the presence of a base such as sodium or potassium hydroxide or carbonate in aqueous methanol or ethanol, or in the presence of an acid such as hydrochloric acid or p-toluenesulphonic acid in aqueous tetrahydrofuran, depending on the nature of $Q_1'$, $Q_2'$, $R_1$ and $R_2$.

Compounds of formula V in which $Q_1'$, $Q_2'$ represent the group

or —(CO)— and $R_2$ represents an easily hydrolysable ester radical are without further conversion compounds of the invention.

Compounds of formula V in which $Q'_1$ and/or $Q'_2$ represent the group

or —(CO)—, and $R_3$ represents an alkanoyl, alkoxyalkyl, aralkanoyl or aroyl radical can be converted to compounds of the invention by hydrolysis in aqueous methanol, ethanol or THF in presence of an acid such as hydrochloric acid, acetic acid and p-toluenesulphonic acid or in anhydrous non-protic organic solvents, e.g. dichloromethane in presence of a Lewis acid, e.g. trimethylsilyl bromide. If $R_3$ represents an alkoxy or an aryloxy radical, compounds of formula V can be converted to compounds of the invention by hydrolysis in aqueous methanol or ethanol and in the presence of a base such as sodium or potassium hydroxide or carbonate.

The compounds of formula V in which $Q_1'$, $Q_2'$ each represent the group

or —(CO)— and $R_2$ represents an unsubstituted or substituted benzyl radical, a cyanomethyl, alkanoylmethyl or aroylmethyl can also be converted into compounds of formula I by reduction. In the case where $R_2$ represents a benzyl or a cyanomethyl radical, catalytic hydrogenation is preferred, whereas, when $R_2$ represents acetonyl, phenacyl or trichloroethyl radical, a reduction with zinc in acetic acid can be used. When $R_2$ is a substituted silyl radical, acid hydrolysis using diluted acids such as hydrochloric acid, acetic acid or toluenesulphonic acid or fluoride assisted cleavage, e.g. hydrogen fluoride in acetonitrile or tetrabutylammonium fluoride in THF can be used.

The compounds of general formula I in which A represents an oxygen may alternatively be prepared by a method comprising a first step in which compounds of the general formula VI are converted into 16-acyloxy or 16-O-alkyl compounds of formula VII as described below:

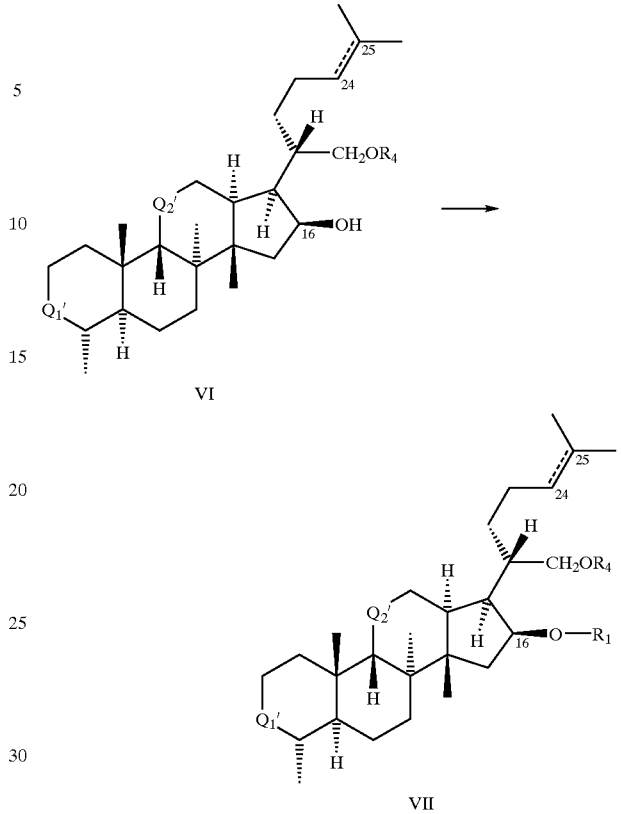

in which formulas $Q_1'$, $Q_2'$, $R_1$ and the dotted line between C-24 and C-25 have the meanings defined above; and $R_4$ represents a common protective group such as alkanoyl, aralkanoyl, alkanoyloxyalkyl or aroyl, or a trisubstituted silyl radical substituted with alkyl, oxyalkyl, aryl or oxyaryl groups.

$R_4$ is preferably a silyl protective group such as diphenylmethylsilyl or tert.butoxydiphenylsilyl, or an acyl protective group such as acetyl or pivaloyl.

For compounds of formula VII in which $R_1$ represents an alkyl radical as defined above, the conversion is performed by reacting a compound of formula VI with an alkylhalide or an alkyltriflate according to general methods of ether preparations known to those skilled in the art. For compounds of formula VII in which $R_1$ represents an acyl group, the conversion is performed by reacting a compound of formula VI with an acylchloride or a corresponding acid anhydrides in presence of a weak base according to general acylation methods known to those skilled in the art. Compounds of formula VII can be converted to compounds of formula I by first removing the $R_4$ protective group by known methods and then by the same reaction steps f and g as described in Scheme 2 or by related methods.

The compounds of formula I wherein $Q_1$ and/or $Q_2$ represent —(CO)— can also be prepared from the corresponding compounds of formula I wherein $Q_1$ and $Q_2$ both represent the group

by oxidation methods known by those skilled in the art.

The invention further relates to a method for producing a compound of formula I wherein the inversion of C-20 is obtained quantitatively by heating the lactone of formula 3 herein in the presence of concentrated sodium hydroxide.

The easily hydrolysable esters of the compounds of formula I and Ia can be prepared in known manner by methods described in the literature.

Compounds of the invention in which C-24 and C-25 are connected by a single bond can be prepared from the corresponding unsaturated analogues by reduction, e.g. by catalytic hydrogenation using catalysts such as palladium or platinum. Compounds such as helvolic acid and cephalosporin $P_1$ may be used as starting materials in the preparation of other compounds of general formula Ia.

Compounds of formula II are prepared starting from compounds in Scheme 1 by methods known from the literature (cf. GB Patent No. 1 490 852 and GB Patent No. 1 523 803) or by analogous methods. Starting compounds of formula III can for instance be prepared from the compound of formula 10 or more conveniently from the compound of formula 9 as outlined in Scheme 3.

It is a further object of the present invention to provide pharmaceutical compositions which are useful in the treatment of infectious diseases in the human and veterinary practice.

With this object in view, the composition of the invention contain as an active component at least one member selected from the group consisting of compounds of formula Ia and formula I (hereinafter referred to as the active ingredient) including acceptable salts and easily hydrolysable esters thereof together with acceptable pharmaceutical carriers and/or diluents.

In said composition, the proportion of therapeutically active material to carrier substance can vary from 0.5% to 95% by weight. The compositions can be worked up to various pharmaceutical forms of presentation such as granulates, tablets, pills, dragees, suppositories, capsules, sustained-release tablets, suspensions, injection and may be filled in bottles or tubes or similar containers. Pharmaceutical organic or inorganic, solid or liquid carriers and/or diluents suitable for oral, enteral, parenteral or topical administration can be used to make up compositions containing the present compounds: Water, gelatine, lactose, starch, magnesium stearate, talc, vegetable and animal oils and fats, benzyl alcohol, gum, polyalkylene glycol, petroleum jelly, cocoa butter, lanolin, and other emulsifying agents, salts for varying the osmotic pressure or buffers for securing an appropriate pH-value of the composition can be used as auxiliary agents.

Furthermore, the composition may contain other therapeutically active components which can appropriately be administered together with the compounds of the invention in the treatment of infectious diseases such as other suitable antibiotics, in particular such antibiotics which may enhance the activity and/or prevent development of resistance. Such antibiotics include penicillins, cephalosporins, tetracyclines, rifamycins, erythromycins, lincomycin, clindamycin and fluoroquinolones. Other compounds which advantageously may be combined with the compounds of the invention, especially in topical preparations, include e.g. corticosteroids, such as hydrocortisone or triamcinolone. Alternatively, such other therapeutically active component(s) may be administered concomitantly (either simultaneously or sequentially) with the composition of the invention.

For granulates, tablets, capsules or dragees the pharmaceutical composition of the invention appropriately contains from 25% to 98% of the active substance of the invention, and in oral suspensions the corresponding amount is appropriately from 2% to 20% active ingredient.

When the compounds are administered in the form of salts with pharmaceutically acceptable non-toxic bases. The preferred salts are for instance easily water-soluble or slightly soluble in water, in order to obtain a particular and appropriate rate of absorption.

As indicated above, the compounds of formula I and Ia and their salts may be worked up to pharmaceutical forms of presentation including suspensions, ointments and creams: A pharmaceutical preparation for oral treatment may also be in form of a suspension of the active ingredient as such or in the form of a sparingly water-soluble pharmaceutically acceptable salt, the preparation containing from 20 to 100 mg per ml of vehicle. A pharmaceutical preparation for topical treatment may be in the form of an ointment or cream containing the active ingredient in an amount of from 0.5 to 50% of preparation. Topical preparations are favourable due to the stability towards sunlight and the relatively lipophilic nature of the present compounds.

Another object of the invention resides in the selection of a dose of the compounds of the invention which dose can be administered so that the desired activity is achieved without simultaneous secondary effects. In the human systemic therapy the compounds and their salts are conveniently administered (to adults) in dosage units containing no less than 50 mg and up to 1000 mg, preferably from 200 to 750 mg, calculated as the compound of formula I.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or, liquid pharmaceutical diluents or carriers.

In the form of a dosage unit, the compound may be administered one or more times a day at appropriate intervals, always depending, however, on the conditions of the patient, and in accordance with the prescription made by the medical practitioner.

Thus in systemic treatment a daily dosage will preferably be an amount of from 0.5 to 3 g of the active ingredient.

The term "usage unit" in connection with topical use means a unitary, i.e. a single dose capable of being administered topically to a patient in an application per square centimeter of the infected area of from 0.1 mg to 10 mg and preferably from 0.2 mg to 1 mg of the active ingredient in question.

If the composition is to be injected, a sealed ampoule, a vial or a similar container may be provided containing a parenterally acceptable aqueous or oily injectable solution or dispersion of the active ingredient as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components as mentioned herein before.

Still another object of the invention is to provide a method of treating patients suffering from infectious diseases, the method comprising administering to patients from 0.03 g to 0.7 g/kg body weight per day in 1 to 3 doses, preferably from 0.5 g to 3 g per day of a compound of formula I or Ia or an equivalent amount of a salt as defined before of a compound of formula I or Ia. Preferably, the active ingredient is given in the form of the dosage units as before said.

The invention will be further described in the following non-limiting Preparations and Examples.

PREPARATIONS AND EXAMPLES

General

All melting points are uncorrected. For $^{13}$C nuclear magnetic resonance (NMR) spectra (75.6 MHz) chemical shift values (δ) (in ppm) are quoted, unless otherwise specified, for deuteriochloroform solutions relative to internal tetramethylsilane (δ=0.00) or deuteriochloroform (δ=76.81 for $^{13}$C NMR). Chromatography was performed on silica gel using ethyl acetate and low boiling petroleum ether as eluant. Anhydrous solvents were prepared by storing analytical grade solvents over 4 Å molecular sieves a few days prior to use.

Preparations

Preparation 1: 16-Deacetyl-17(S),20(S)-dihydrofusidic Acid Lactone (4)

Lactone 3 (20.2 g, 44 mmol) was dissolved in 100 ml ethanol and a 28% aqueous solution of sodium hydroxide (100 ml) was added. The resulting yellow solution was heated at 60° C. for 1 hour. The reaction mixture was allowed to attain room temperature and the mixture was acidified to pH 4 with concentrated acetic acid resulting an almost colourless solution. Water (ca. 100 ml) was added slowly under continuos stirring until precipitation of colourless crystals. Stirring was continued overnight at room temperature and crystals were collected by filtration yielding 20.0 g of 16-deacetyl-17(S),20(S)-dihydrofusidic acid lactone (4). Recrystallisation from methanol-water afforded 18.5 g, melting point 167–169° C.

$^{13}$C NMR (CDCl$_3$): 181.0, 132.9, 122.9, 84.2, 71.4, 68.7, 49.7, 48.7, 46.8, 42.4, 41.4, 40.0, 38.8, 37.4, 36.6, 36.1, 33.9, 33.0, 32.9, 30.4, 30.0, 25.7, 25.7, 23.8, 22.6, 21.0, 17.8, 17.5, 16.0.

Preparation 2: 3,11-Bis-O-methoxymethyl-16-deacetyl-17(S),20(S)-dihydrofusidic Acid Lactone (5)

Lactone (4) (34.4 g, 75 mmol) was dissolved in anhydrous dichloromethane (350 ml) under argon in a an oven-dried two-necked round bottom flask fitted with a condenser. N,N-Diisopropylethylamine (52.3 ml, 300 mmol) was added and the resulting solution was stirred for 5 min at room temperature prior to addition of methoxymethylchloride (22.8 ml, 300 mmol) which was slowly injected by a syringe. The reaction mixture was stirred for 15 min at room temperature and then at reflux until completion of the reaction as monitored by TLC (about 4 hours). The reaction mixture was allowed to attain room temperature and transferred to a separatory funnel with 650 ml dichloromethane. The organic solution was washed successively with water (500 ml), saturated sodium bicarbonate (500 ml), twice with water (2×200 ml) and twice with brine (2×500 ml). The organic solution was dried over anhydrous sodium sulphate concentrated in vacuo yielding a yellow oil which crystallised upon standing. The crystalline compound was recrystallised from hot methanol (200 ml). Colourless crystals were collected by filtration affording 31.5 g of 3,11-bis-O-methoxymethyl-16-deacetyl-17(S),20(S)-dihydrofusidic acid lactone (5), melting point 123–125° C. Crystallisation of the mother liquour afforded further 6.5 g of the same compound, melting point 119–121° C.

$^{13}$C NMR (CDCl$_3$): 180.9, 132.8, 123.0, 97.6, 95.3, 84.3, 77.7, 77.2, 55.8, 55.4, 50.1, 48.5, 47.1, 42.6, 41.6, 40.0, 39.4, 37.1, 36.9, 36.4, 34.0, 32.3, 30.2, 30.1, 26.8, 25.9, 25.7, 23.3, 23.1, 21.3, 17.8, 17.7, 16.1

Preparation 3: 16β,21-Diol (6)

Lithium aluminium hydride (3.8 g, 100 mmol) was suspended in anhydrous THF (175 ml) under argon in a an oven-dried two-necked round bottom flask fitted with a condenser. To the stirred suspension was added a solution of lactone (5) (26.7 g, 48.9 mmol) in anhydrous THF (150 ml) in such a rate causing gentle reflux. The reaction mixture was refluxed under vigorous stirring for 3 hours and then allowed to attain room temperature. Excess lithium aluminium hydride was destroyed with ethyl acetate (125 ml) and then water (125 ml) was added slowly. The resulting suspension was acidified with diluted hydrochloric acid to pH 5. The suspension was transferred to a separatory funnel with ethyl acetate (1000 ml) and water. (750 ml). The two layers were shaken well and separated. The aqueous layer was extracted with ethyl acetate (1000 ml) and the combined organic layers were washed twice with brine (2×500 ml). The organic layer was dried over anhydrous sodium sulphate and concentrated in vacuo yielding 26.6 g of essentially pure title compound diol (6) as a colourless powder. An analytically pure sample was obtained by recrystallisation from hot methanol, melting point 120–131° C.

$^{13}$C NMR, (CDCl$_3$): 131.5, 124.5, 97.3, 95.3, 78.0, 77.3, 74.7, 64.8, 55.7, 55.4, 50.5, 49.1, 48.5, 43.5, 41.3, 40.5, 39.5, 36.9, 36.6, 32.0, 31.8, 31.4, 30.0, 26.8, 25.9, 25.7, 23.5, 22.9, 21.5, 18.6, 17.7, 16.1

Preparation 4: 21-Diphenylmethylsilyl-protected 16β,21-diol (7)

Diol (6) (5.5 g, 10 mmol) was dissolved in anhydrous dichloromethane (50 ml) and triethylamine (2.8 ml, 20 mmol) under argon in a an oven-dried two-necked round bottom flask and cooled at −10° C. To the cooled solution was added over a period of 15 min a solution of diphenylmethylchlorosilane (2.3 ml, 11 mmol) in anhydrous dichloromethane (20 ml) so that the temperature did not exceed 0° C. and stirring was continued for 15 min. The reaction mixture was transferred to a separatory funnel and diluted with 100 ml dichloromethane. The organic solution was washed successively with saturated sodium bicarbonate (100 ml), water (100 ml) and brine (100 ml). The organic solution was dried over anhydrous sodium sulphate and solvents were evaporated under reduced pressure yielding 9 g of a colourless syrup. The crude mixture was without purification acetylated by dissolving in pyridine (15 ml) and acetic anhydride (15 ml). The resulting mixture was stirred overnight at room temperature in a stoppered bottle. After this time the reaction mixture was concentrated in vacuo yielding a pale yellow oil. Essentially pure title compound (7), 6.2 g, was obtained as a colourless syrup after column chromatography using a mixture of ethyl acetate and low boiling petroleum ether as eluant.

$^{13}$C NMR, (CDCl$_3$): 170.1, 134.2, 129.5, 127.6, 124.6, 97.1, 95.0, 77.6, 77.1, 77.0, 64.9, 55.5, 55.1, 50.0, 48.3, 42.5, 40.9, 40.6, 38.9, 36.7, 36.3, 36.2, 31.7, 31.2, 30.3, 29.8, 26.6, 25.6, 25.5, 23.1, 22.8, 21.2, 21.1, 17.8, 17.5, 15.9, 14.0, −3.3

Preparation 5: 16β,21-Diol 16-acetate (8)

21-Diphenylmethylsilyl-protected 16β,21-diol (7) (6.2 g, 7.9 mmol) was dissolved in tetrahydrofuran (100 ml) and glacial acetic acid (0.75 ml). To this solution was added tetrabutyl ammonium fluoride hydrate (4 g, 15.8 mmol) and the reaction mixture was stirred at room temperature for 10 min. The reaction mixture was then transferred to a separatory funnel with 200 ml ethyl acetate. The organic solution was washed twice with water (2×100 ml) and brine (100 ml). The organic layer was dried over anhydrous sodium sulphate and concentrated in vacuo yielding a colourless syrup. Pure title compound (8), 4.3 g, was obtained as a colourless syrup after column chromatography using a mixture of ethyl acetate and low boiling petroleum ether as eluant.

$^{13}$C NMR, (CDCl$_3$): 170.3, 131.7, 124.4, 97.4, 95.3, 77.9, 77.3, 64.9, 55.8, 55.4, 50.4, 48.6, 43.7, 41.3, 40.8, 39.1, 37.0, 36.6, 36.5, 31.9, 31.6, 30.9, 30.1, 26.8, 25.9, 25.7, 23.4, 23.1, 21.6, 21.3, 18.3, 17.8, 16.1.

Preparation 6: 3,11-Bis-O-methoxymethyl-17(S),20 (S)-dihydrofusidic Acid (9)

Dess-Martin periodinane (3.7 g, 8.7 mmol) dissolved in anhydrous dichloromethane (60 ml) was added to a solution of 16β,21-diol 16-acetate (8) (4 g, 6.7 mmol) in dichloromethane (50 ml) under or at room temperature. The reaction mixture was stirred for 15 min. After this time 1N sodium bicarbonate (50 ml) and 1N 1N sodium thiosulfate (50 ml) were poured into the reaction mixture and the two layers were vigorously stirred for 10 min. The two layers were transferred to a separatory funnel with ethyl acetate (100 ml). The two layers were separated and the organic layer was washed with saturated sodium bicarbonate (100 ml) and brine (100 ml). The organic layer was dried over anhydrous sodium sulphate and concentrated in vacuo yielding 3.7 g of a colourless syrup. The crude aldehyde (3.7 g, 6.2 mmol) was without purification dissolved in tert-butanol (50 ml). To this solution was added 2-methyl-2-butene (1.48 ml, 16.8 mmol), 1N sodium dihydrogenphosphate (16 ml) and sodium chlorite (1.44 g, 16 mmol) in water (20 ml) and the resulting reaction mixture was stirred vigorously for ca. 3 hours at room temperature. The reaction mixture was acidified to pH 4 with acetic acid and transferred to a separatory funnel with ethyl acetate (200 ml). The two layers were shaken and separated. The aqueous layer was re-extracted twice with ethyl acetate (2×100 ml). The combined organic extracts were washed twice with brine (2×100 ml), dried over anhydrous sodium sulphate and concentrated in vacuo yielding 3.4 g of a pale yellow foam. Purification by column chromatography using a mixture of ethyl acetate, low boiling petroleum ether and a trace of formic acid as eluant yielded 2.9 g of pure acid 9, the title compound, as a semicrystalline compound.

$^{13}$C NMR, (CDCl$_3$): 182.2, 170.1, 132.4, 123.2, 97.6, 95.3, 77.9, 77.3, 76.4, 55.8, 55.4, 49.9, 49.1, 45.2, 44.5, 40.9, 40.6, 38.8, 36.9, 36.6, 36.5, 32.6, 31.9, 31.5, 30.1, 26.8, 25.7, 25.2, 23.4, 23.2, 21.2, 20.6, 17.7, 17.6, 16.1

Preparation 7: 3,11-Bis-O-methoxymethyl-17(S),20 (S)-dihydrofusidic Acid Tert-butyl Ester (17)

3,11-Bis-O-methoxymethyl-17(S),20(S)-dihydrofusidic acid (9) (6.2 g, 10.8 mmol) was dissolved in anhydrous benzene (40 ml): The solution was heated at reflux and N,N-dimethylformamide tert-butyl acetate (10.4 ml, 43.2 mmol) dissolved in anhydrous benzene (20 ml) was added over a period 4 hours. The reaction was refluxed for a further 1 hour, cooled, transferred to a separatory funnel and diluted with ethyl acetate (150 ml). The organic solution was washed with water (30 ml), saturated aqueous sodium bicarbonate (30 ml) and brine (30 ml). The organic layer was dried over anhydrous sodium sulphate and concentrated in vacuo to yield a colourless foam which was purified by column chromatography on silica gel affording the title compound tert-butyl ester 17 as a colourless foam.

$^{13}$C NMR, (CDCl$_3$): 174.3, 170.5, 131.9, 123.8, 97.6, 95.3, 79.8, 77.9, 77.3, 77.2, 55.8, 55.4, 49.7, 49.2, 47.3, 43.8, 40.9, 40.7, 39.0, 36.9, 36.7, 36.3, 32.5, 32.0, 31.5, 30.1, 28.0, 26.8, 25.7, 25.2, 23.4, 23.2, 21.5, 21.2, 17.8, 17.7, 16.1

Preparation 8: 3,11-Bis-O-methoxymethyl-16-deacetyl-17(S),20(S)-dihydrofusidic Acid Tert-butyl Ester (18)

Tert-butyl ester 17 (4 g, 6.8 mmol) was dissolved in ethanol and 4N aqueous sodium hydroxide (10 ml). The resulting mixture was refluxed for 1 h, cooled and acidified to pH 4 with hydrochloric acid. Water (50 ml) and ethyl acetate (50 ml) were added and the mixture was transferred to a separatory funnel. The two layers were separated and the aqueous layer was re-extracted thrice with ethyl acetate 3×50 ml). The combined organic layers were dried over anhydrous sodium sulphate and concentrated in vacuo to yield the title compound tert-butyl ester (18).

Preparation 9: 3,11-Bis-O-methoxymethyl-16-deacetoxy-16α-bromo-17(S),20(S)-dihydrofusidic Acid Tert-butyl Ester (19)

Tert-butyl ester (18) (2 g, 3.4 mmol) and tetrabromomethane (1.32 g, 4 mmol) were dissolved in dichloromethane (50 ml) and cooled at 0° C. To the cooled solution was added in small portions solid triphenylphosphine (1.05 g, 4 mmol). The reaction was quenched after one hour by adding triethylamine (3 ml). Diethyl ether (50 ml) was added to precipitate triphenylphosphine oxide which was then filtered off. The organic solution was transferred to a separatory funnel and washed with water (20 ml), saturated sodium bicarbonate (20 ml) and brine (20 ml). The organic solution was dried over anhydrous sodium sulphate concentrated in vacuo yielding the title compound tert-butyl ester (19).

Preparation 10: 3-O-TBS-16-deacetyl-17(S),20(S)-dihydrofusidic Acid Lactone (11)

Lactone (4) (15.25 g, 33.2 mmol) was dissolved in anhydrous DMF (75 ml) under argon in a an oven-dried two-necked round bottom flask. To the solution was added imidazol (4.5 g, 66.4 mmol) and then TBSCl (10 g, 66.4 mmol). The resulting pale yellow reaction mixture was stirred overnight at room temperature. The reaction mixture was diluted with ethyl acetate and washed successively with water and brine. The organic solution was dried over anhydrous sodium sulphate and concentrated in vacuo yielding a yellow oil which crystallised upon standing. The crystalline compound was recrystallised from methanol (100 ml). Colourless crystals were collected by filtration affording 14.7 g 3-O-TBS-16-deacetyl-17(S),20(S)-dihydrofusidic acid lactone (11), melting point 138.5–140° C.

Preparation 11: 16β,21-Diol (12)

Lithium aluminium hydride (2.5 g, 65 mmol) was suspended in anhydrous THF (125 ml) under argon in a an oven-dried two-necked round bottom flask fitted with a condenser. To the stirred suspension was added a solution of lactone 11 (18.4 g, 32.1 mmol) in anhydrous THF (75 ml) in such a rate causing gentle reflux. The reaction mixture was refluxed under vigorous stirring for 4 hours and then allowed to attain room temperature. Excess lithium aluminium hydride was destroyed with ethyl acetate (125 ml) and then water (125 ml) was added slowly. The resulting suspension was acidified with diluted hydrochloric acid to pH 5. The suspension was transferred to a separatory funnel with ethyl acetate (500 ml) and water (400 ml). The two layers were shaken well and separated. The aqueous layer was extracted with ethyl acetate (500 ml) and the combined organic layers were washed twice with brine (2×500 ml). The organic layer was dried over anhydrous sodium sulphate and concentrated in vacuo yielding 19 g of almost pure title compound diol (12) as a colourless powder. Diol was crystallised from methanol-water and colourless crystals were collected by filtration affording 14.7 g of diol (12) after freeze drying, melting point 122–124° C.

Preparation 12: 21-Diphenylmethylsilyl-protected 16β,21-diol (13)

Diol (12) (14.05 g, 24.4 mmol) was dissolved in anhydrous dichloromethane (125 ml) and triethylamine (6.8 ml, 48.8 mmol) under argon in a an oven-dried two-necked round bottom flask and cooled at −20° C. To the cooled solution was added over a period of 1 hour a solution of diphenylmethylchlorosilane (25.7 ml, 26.8 mmol) in anhydrous dichloromethane (50 ml). Stirring was continued for 15 min. The reaction mixture was transferred to a separatory funnel and diluted with 500 ml dichloromethane. The organic solution was washed successively with saturated sodium bicarbonate (250 ml), water (250 ml) and brine (250 ml). The organic solution was dried over anhydrous sodium sulphate and solvents were evaporated under reduced pressure yielding 17 g of a colourless syrup. The crude pale yellow syrup was purified by column chromatography using a mixture of ethyl acetate and low boiling petroleum ether as eluant yielding 14.7 g 21-diphenylmethylsilyl-protected 16β,21-diol (13) as a colourless foam.

Preparation 13: Compound 14

21-Diphenylmethylsilyl-protected 16β,21-diol (13) (9 g, 11.0 mmol) was acetylated by dissolving in pyridine (30 ml) and acetic anhydride (15 ml). The resulting mixture was stirred 20 hours at room temperature in a stoppered bottle. After this time the reaction mixture was concentrated in vacuo yielding 11 g of a pale yellow oil. Column chromatography using a mixture of ethyl acetate and low boiling petroleum ether as eluant yielded 7.9 g of pure acetylated compound (14).

Preparation 14: 16β,21-Diol 16-acetate (15)

Compound 14 (7.5 g, 9.2 mmol) was dissolved in 100 ml THF. To the solution was added acetic acid (3.2 ml) and TBAF (4.69 g, 18.4 mmol) and the resulting reaction mixture was stirred for 5 min at room temperature. After this time water (100 ml) and ethyl acetate (200 ml) were added and the two layers were transferred to a separatory funnel. The two layers were separated and the aqueous layer was reextracted with EtOAc (200 ml). The combined organic layers were washed twice with water (2×100 ml) and brine (100 ml). The organic layer was dried over anhydrous sodium sulphate and concentrated in vacuo yielding a colourless syrup. Pure title compound (15), 5.7 g, was obtained as a colourless syrup after column chromatography using a mixture of ethyl acetate and low boiling petroleum ether as eluant.

Preparation 15: 3-O-TBS-17(S),20(S)-dihydrofusidic Acid (16)

A. To a solution of 16β,21-diol 16-acetate (15) (5.4 g, 8.75 mmol) in anhydrous THF (125 ml) cooled at 0° C. was added Dess-Martin periodinane (3.72 g, 8.75 mmol) in small portions over 1 hour. The reaction mixture was stirred for 3 hours at 0° C. After this time 1N sodium bicarbonate (90 ml) and 1N sodium thiosulfate (90 ml) were poured into the reaction mixture and the two layers were vigorously stirred for 10 min. The two layers were transferred to a separatory funnel with dichloromethan (400 ml). The two layers were separated and the organic layer was washed with saturated sodium bicarbonate (200 ml) and water (200 ml). The organic layer was dried over anhydrous sodium sulphate and concentrated in vacuo yielding 5.4 g of a syrup. Pure aldehyde, 5.0 g, was obtained as a colourless syrup after column chromatography using a mixture of ethyl acetate and low boiling petroleum ether as eluant.

B. The aldehyde from preparation 15A (5.18 g, 8.4 mmol) was without purification dissolved in tert-butanol (50 ml). To this solution was added 2-methyl-2-butene (3.55 ml, 33.6 mmol), 1N sodium dihydrogenphosphate (34 ml) and sodium chlorite (3.84 g, 34 mmol) in water (20 ml) and the resulting reaction mixture was stirred vigorously overnight at room temperature. The reaction mixture was acidified to pH 4 with acetic acid and transferred to a separatory funnel with ethyl acetate (200 ml). The two layers were shaken and separated. The aqueous layer was re-extracted twice with ethyl acetate (2×200 ml). The combined organic extracts were washed twice with brine (2×100 ml), dried over anhydrous sodium sulphate and concentrated in vacuo yielding 6 g of a pale yellow foam. Purification by column chromatography using a mixture of ethyl acetate, low boiling petroleum ether and a trace of formic acid as eluant yielded 4.2 g of pure acid (16), the title compound, as a semi-crystalline compound.

EXAMPLES

Example 1

17(S),20(S)-Dihydrofusidic Acid (10) (Compound 101)

The compound of formula 9 (2 g, 3.3 mmol) was dissolved in anhydrous dichloromethane (50 ml) under argon in an oven-dried two-necked round bottom flask and cooled at −20° C. To the solution was added 4 Å molecular sieves (6 g) and trimethylbromosilane (2.7 ml, 20 mmol) was slowly injected under continuos stirring. The reaction mixture was stirred until completion of the reaction (ca. 5 hours). The reaction mixture was then transferred to a separatory funnel with ethyl acetate and water and the two layers were shaken and separated. The aqueous layer was extracted thrice with ethyl acetate (3×20 ml) and the combined organic layers were washed with brine (30 ml). The organic solution was dried over anhydrous sodium sulphate and concentrated in vacuo yielding 1.4 g of compound 101 as a colourless solid. Recrystallisation from methanol-water yielded 1.2 g of colourless crystals, M.p. 195–195.5° C.

$^{13}$C NMR, (CD$_3$OD), 173.1, 131.8, 126.2, 78.3, 72.6, 69.4, 50.8, 50.6, 46.6, 41.9, 41.8, 39.6, 38.2, 38.0, 37.1, 36.2, 35.2, 33.1, 31.1, 27.2, 25.9, 23.7, 23.6, 22.6, 21.2, 17.9, 16.5

Example 1a

Alternative Preparation of 17(S),20(S)-dihydrofusidic Acid (10) (Compound 101)

The compound of formula 16 (3.6 g, 5.7 mmol) was dissolved in THF (15 ml) and 40% aqueous hydrogen fluoride (10 ml) in a round bottom teflon flask. The resulting reaction mixture was stirred at room temperature for two days. The reaction was then neutralised to pH 8 with a 27% sodium hydroxide solution and finally adjusted to pH 4 with acetic acid. The reaction mixture was then transferred to a separatory funnel with ethyl acetate and water and the two layers were shaken and separated. The aqueous layer was extracted thrice with ethyl acetate (3×50 ml) and the combined organic layers were washed with brine (50 ml). The organic solution was dried over anhydrous sodium sulphate and concentrated in vacuo yielding 4 g of crude 101 as a colourless solid. Purification by column chromatography using a mixture of ethyl acetate, low boiling petroleum ether and a trace of formic acid as eluant yielded 3.1 g of pure 17(S),20(S)-dihydrofusidic acid (10) (Compound 101), the title compound, as a crystalline compound. Recrystallisation from methanol-water yielded 2.9 g of colourless crystals, M.p. 195–196° C.

$^{13}$C NMR, (CD$_3$OD), 173.1, 131.8, 126.2, 78.3, 72.6, 69.4, 50.8, 50.6, 46.6, 41.9, 41.8, 39.6, 38.2, 38.0, 37.1, 36.2, 35.2, 33.1, 31.1, 27.2, 25.9, 23.7, 23.6, 22.6, 21.2, 17.9, 16.5

Example 2

17(S),20(S),24,25-Tetrahydrofusidic Acid (Compound 102)

A solution of compound 101 (280 mg, 0.54 mmol) in ethanol (3 ml) was hydrogenated under 1 atmosphere of hydrogen in the presence of 5% palladium on calcium carbonate (30 mg). The reaction mixture was stirred vigorously until the theoretical amount of hydrogen was consumed and the catalyst was removed by filtration. Water was added dropwise to the filtrate yielding 255 mg crystalline 17(S),20(S),24,25-tetrahydrofusidic acid. M.p. 138.5–140° C.

$^{13}$C NMR, (DMSO-d$_6$): 210.7, 176.6, 169.1, 131.2, 123.7, 75.3, 69.0, 57.7, 48.9, 43.8, 43.6, 43.3, 41.8, 41.7, 37.7, 37.2, 34.4, 32.6, 30.1, 27.9, 25.3, 24.8, 22.7, 20.6, 20.4, 20.1, 17.4, 16.3, 16.0

Example 3

11-Dehydro-17(S),20(S)-dihydrofusidic Acid (Compound 103)

A. 3-O-Formyl-17(S),20(S)-dihydrofusidic acid

17(S),20(S)-Dihydrofusidic acid (260 mg, 0.5 mmol) was dissolved in a solution of mixed anhydrides prepared from acetic anhydride and formic acid (2:1, v/v) at 5° C.→50° C. containing formic anhydride, dichloromethane (4.4 ml) and dimethylaminopyridine (30 mg) and stirred at room temperature for 20 hours. The mixture was concentrated in vacuo and the oily residue was dissolved in ethyl acetate (25 ml), washed with water (10 ml) and brine (10 ml). The organic layer was dried over anhydrous sodium sulphate and concentrated in vacuo yielding 250 mg 3-O-formyl-17(S),20(S)-dihydrofusidic acid as an oily product which crystallised upon standing.

B. 3-O-Formyl-11-dehydro-17(S),20(S)-dihydrofusidic acid

To the crude 3-O-formyl-17(S),20(S)-dihydrofusidic acid from A, dissolved in acetic acid (2.5 ml) was added a solution of chromic acid (65 mg, 0.65 mmol) in water (0.65 ml), and the resulting green reaction mixture was stirred for 3 hours at room temperature. The reaction mixture was diluted with diethyl ether (40 ml), washed with water (20 ml) and twice with brine (2×10 ml), dried over anhydrous sodium sulphate and concentrated in vacuo yielding 255 mg of 3-O-formyl-11-dehydro-17(S),20(S)-dihydrofusidic acid as a colourless oil.

C. 11-Dehydro-17(S),20(S)-dihydrofusidic acid

To a solution of crude 3-O-formyl-11-dehydro-17(S),20(S)-dihydrofusidic acid from B in methanol (3 ml) cooled at 0° C. was added solid potassium carbonate (130 mg) and the resulting suspension was stirred vigorously for 1 hour. The reaction mixture was acidified to pH 3 with 2N hydrochloric acid, diluted with ethyl acetate (40 ml), transferred to a separatory funnel and washed with water (15 ml) and twice with brine (2×10 ml). The organic layer was dried over anhydrous sodium sulphate and concentrated in vacuo yielding a pale yellow oily product which was purified by column chromatography using mixtures low boiling petroleum ether, ethyl acetate with a trace of formic acid as eluant. Colourless semi-crystalline product of 11-dehydro-17(S),20(S)-dihydrofusidic acid were obtained from methanol-water.

$^{13}$C NMR, (CD$_3$OD): 180.5, 172.1, 77.9, 72.5, 69.2, 50.8, 50.6, 47.2, 46.2, 41.8, 40.2, 39.6, 38.2, 38.0, 37.0, 36.0, 34.5, 33.0, 31.1, 29.1, 25.7, 23.7, 23.6, 23.1, 23.0, 22.6, 20.8, 17.7, 16.5

Example 4

3-Dehydro-17(S),20(S)-dihydrofusidic Acid (Compound 104)

17(S),20(S)-Dihydrofusidic acid (260 mg, 0.5 mmol) was dissolved in tetrahydrofuran (10 ml) and cooled at 0° C. Solid Dess-Martin periodinane (250 mg, 0.59 mmol) was added in small portions and the reaction was stirred for 5 hours. The reaction mixture was diluted with ethyl acetate (40 ml) and transferred to a separatory funnel. The organic solution was shaken vigorously with 10% aqueous sodium thiosulphate (15 ml), washed with water (10 ml) and brine (10 ml). The organic layer was dried over anhydrous sodium sulphate and concentrated in vacuo affording a colourless syrup. Purification by column chromatography using mixtures of petroleum ether-ethyl acetate-formic acid as eluant yielded 215 mg of 3-dehydro-17(S),20(S)-dihydrofusidic acid.

Example 5

16-Deacetoxy-16β-propionyloxy-17(S),20(S)-dihydrofusidic Acid (Compound 105)

A. 3,11-Bis-O-methoxymethyl-16-deacetoxy-16β-propionyloxy-17(S),20(S)-dihydrofusidic acid.

Compound 18 (288 mg, 0.5 mmol) was dissolved in a mixture of dichloromethane (2 ml), propionic anhydride (2 ml) and pyridine (2 ml) and stirred overnight at room temperature. Solvents were evaporated in vacuo to yield a colourless oil of essentially pure 3,11-bis-O-methoxymethyl-16-deacetoxy-16β-propionyloxy-17(S),20(S)-dihydrofusidic acid.

B. 16-Deacetoxy-16β-propionyloxy-17(S),20(S)-dihydrofusidic acid.

To a solution of the tert-butyl ester from A in tetrahydrofuran (5 ml) was added 2N aqueous hydrochloric acid (5 ml) and stirred at room temperature overnight. The reaction mixture was then diluted with ethyl acetate (25 ml) and transferred to a separatory funnel. The two layers were separated and the organic layer was washed twice with water (2×5 ml) and twice with brine (2×5 ml). The organic layer was dried over sodium sulphate and concentrated in vacuo to yield 16-deacetoxy-16β-propionyloxy-17(S),20(S)-dihydrofusidic acid.

$^{13}$C NMR, (CDCl$_3$): 180.9, 173.4, 132.4, 123.3, 76.2, 71.4, 68.8, 49.4, 45.2, 44.3, 40.7, 40.6, 38.3, 37.2, 36.4, 36.2, 34.4, 32.8, 32.6, 30.4, 30.0, 27.4, 25.7, 25.4, 23.9, 22.6, 20.9, 17.7, 17.3, 15.9, 8.9

Example 6

16-Deacetoxy-16β-(3'-chloropropionyloxy)-17(S),20(S)-dihydrofusidic Acid (Compound 106)

A. 3,11-Bis-O-methoxymethyl-16-deacetoxy-16β-(3'-chloropropionyloxy)-17(S),20(S)-dihydrofusidic acid tert-butyl ester.

To compound 18 (588 mg, 1 mmol) dissolved in pyridine (3 ml) was added 3-chloropropionyl chloride (0.29 ml, 3 mmol) and the mixture was stirred overnight at room temperature. Solvents were evaporated in vacuo to yield a colourless oil of essentially pure 3,11-bis-O-methoxymethyl-16-deacetoxy-16β-(3'-chloropropionyloxy)-17(S),20(S)-dihydrofusidic acid tert-butyl ester.

B. 16-Deacetoxy-16β-(3'-chloropropionyloxy)-17(S),20(S)-dihydrofusidic acid.

To a solution of the tert-butyl ester from A in tetrahydrofuran (5 ml) was added 2N aqueous hydrochloric acid (5 ml) and stirred at room temperature overnight. The reaction mixture was then diluted with ethyl acetate (25 ml) and transferred to a separatory funnel. The two layers were separated and the organic layer was washed twice with water (2×5 ml) and twice with brine (2×5 ml). The organic layer was dried over sodium sulphate and concentrated in vacuo to yield 16-deacetoxy-16β-(3'-chloropropionyloxy)-17(S),20(S)-dihydrofusidic acid.

Example 7–14

16-Deacetoxy-16β-acyloxy-17(S),20(S)-dihydrofusidic Acids (Compounds 107–114)

A. 16β-Acyloxy derivatives of 3,11-bis-O-methoxymethyl-16-deacetoxy-17(S),20(S)-dihydrofusidic acid tert-butyl ester By following the procedure given in Example 6 A and substituting the acyl chlorides listed in Table 3 for the 3-chloropropionyl chloride, the 16β-acyloxy derivatives of 3,11-bis-O-methoxymethyl-16-deacetoxy-17(S),20(S)-dihydrofusidic acid tert-butyl ester indicated in Table 3 were prepared.

TABLE 3

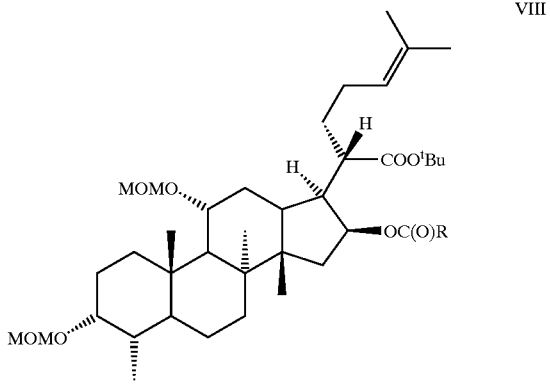

VIII

| Example | Acyl chloride | Resulting compound, R |
|---|---|---|
| 7A | 2'-methylpropionyl chloride | CH(CH$_3$)$_2$ |
| 8A | Cyclopropylcarbonyl chloride | C$_3$H$_5$ |
| 9A | Chloroacetyl chloride | CH$_2$Cl |
| 10A | Bromoacetyl chloride | CH$_2$Br |
| 11A | Benzoyl chloride | C$_6$H$_5$ |
| 12A | 4-Fluorobenzoyl chloride | C$_6$H$_4$F |
| 13A | Cyclohexylcarbonyl chloride | C$_6$H$_{11}$ |
| 14A | Acryloyl chloride | CH=CH$_2$ |

B. 16β-Acyloxy derivatives of 16-deacetoxy-17(S),20(S)-dihydrofusidic acid.

By following the procedure of Example 6B and replacing 3,11-bis-O-methoxymethyl-16-deacetoxy-16β-(3'-chloropropioxy)-17(S),20(S)-dihydrofusidic acid tert-butyl ester with the 16β-acyloxy esters of 3,11-bis-O-methoxymethyl-16-deacetoxy-17(S),20(S)-dihydrofusidic acid tert-butyl ester listed in Table 2, the 16-deacetoxy-16β-acyloxy-17(S),20(S)-dihydrofusidic acids shown in Table 4 were prepared.

TABLE 4

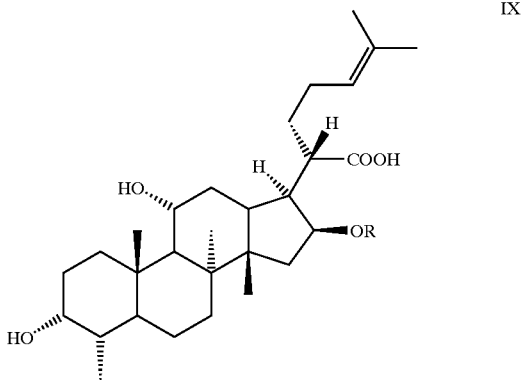

IX

| | | Resulting compound | |
|---|---|---|---|
| Example | No. | R | |
| 7B | 107 | 2'-methylpropionyl | |
| 8B | 108 | cyclopropylcarbonyl | |
| 9B | 109 | chloroacetyl | |
| 10B | 110 | bromoacetyl | |
| 11B | 111 | benzoyl | |
| 12B | 112 | 4'-fluorobenzoyl | |
| 13B | 113 | Cyclohexylcarbonyl | |
| 14B | 114 | Acryloyl | |

¹³C NMR data for compound 107–113:

Compound 107, ¹³C NMR, (CD₃OD): 180.7, 175.9, 132.3, 123.4, 76.3, 71.4, 68.8, 49.4, 45.2, 44.0, 40.8, 40.6, 38.3, 37.2, 36.4, 36.2, 34.5, 33.6, 32.7, 32.6, 30.4, 30.0, 25.7, 25.3, 23.9, 22.7, 20.9, 19.1, 18.1, 17.8, 17.5, 15.9

Compound 108, ¹³C NMR, (CHCl₃): 180.3, 173.9, 132.3, 123.4, 76.4, 71.4, 68.9, 49.4, 45.2, 44.3, 440.7, 40.6, 38.3, 37.2, 36.4, 36.2, 34.5, 32.7, 32.6, 30.4, 30.0, 25.7, 25.4, 23.9, 22.7, 21.0, 17.7, 17.4, 15.9, 12.7, 8.0

Compound 109, ¹³C NMR, (CD₃OD): 180.1, 168.0, 133.2, 124.7, 79.9, 72.5, 69.1, 50.8, 50.7, 46.7, 46.2, 41.8, 41.7, 41.6, 39.7, 38.1, 38.0, 37.1, 35.9, 34.4, 33.1, 31.1, 26.4, 25.9, 23.7, 23.6, 22.5, 17.8, 17.7, 16.5

Compound 110, ¹³C NMR, (CHCl₃): 180.5, 166.4, 154.3, 132.4, 123.3, 78.7, 71.5, 68.8, 49.5, 49.3, 45.2, 44.5, 40.7, 40.6, 38.4, 37.2, 36.4, 36.2, 34.3, 32.7, 32.5, 30.4, 29.9, 25.7, 25.4, 23.8, 22.7, 20.9, 17.7, 17.4, 15.9

Compound 111, ¹³C NMR, (CD₃OD): 179.8, 167.2, 134.1, 133.1, 131.6, 131.0, 129.4, 124.9, 78.7, 72.5, 69.2, 50.8, 50.7, 46.7, 45.9, 42.2, 41.9, 39.8, 38.1, 38.0, 37.1, 36.1, 34.4, 33.1, 31.1, 26.3, 25.9, 23.7, 23.6, 22.5, 18.1, 17.8, 16.5

Compound 112, ¹³C NMR, (CD₃OD): 179.8, 166.2, 167.3, 133.8, 133.1, 128.0,124.8, 116.3, 78.9, 72.5, 69.2, 50.8, 50.7, 46.7, 46.0, 42.1, 41.9, 39.8, 38.1, 38.0, 37.1, 36.1, 34.4, 33.1, 31.1, 26.4, 25.9, 23.7, 23.6, 22.5, 18.2, 17.8, 16.5

Compound 113, ¹³C NMR, (CHCl₃): 180.0, 174.9, 132.3, 123.4, 76.1, 71.4, 68.8, 49.4, 49.3, 45.2, 44.0, 42.7, 40.9, 40.5, 38.4, 37.2, 36.4, 36.1, 34.5, 32.7, 30.4, 30.0, 29.1, 28.1, 25.8, 25.7, 25.3, 25.1, 23.9, 22.6, 20.9, 17.8, 17.5, 15.9

Example 15

16-Deacetoxy-16β-isopropylthio-17(S),20(S)-dihydrofusidic Acid (Compound 115)

A. 3.11-Bis-O-methoxymethyl-16-deacetoxy-16β-isopropylthio-17(S),20(S)-dihydrofusidic acid tert-butyl ester 3,11-Bis-O-methoxymethyl-16-deacetoxy-16α-bromo-17(S),20(S)-dihydrofusidic acid tert-butyl ester (19) (700 mg, 1 mmol) was added to a solution of potassium hydroxide (250 mg) and isopropyl mercaptane (0.75 ml, 8 mmol) in ethanol (25 ml) and the suspension was stirred for four days. After this time, water (ca. 10 ml) was added to complete the precipitation of the desired compound. The the precipitate was collected by filtration and washed with a cold mixture of ethanol and water (2:1) and dried to give 3,11-bis-O-methoxymethyl-16-deacetoxy-16β-isopropylthio-17(S),20(S)-dihydrofusidic acid tert-butyl ester.

B. 16-Deacetoxy-16β-isopropylthio-17(S),20(S)-dihydrofusidic acid

To a solution of the above tert-butyl ester in tetrahydrofuran (5 ml) was added 2N aqueous hydrochloric acid (5 ml) and stirred overnight at room temperature. The reaction mixture was diluted with ethyl acetate (25 ml) and transferred to a separatory funnel. The two layers were separated and the organic layer was washed twice with water (2×5 ml) and twice with brine (2×5 ml). The organic layer was dried over sodium sulphate and concentrated in vacuo to yield 16-deacetoxy-16β-isopropylthio-17(S),20(S)-dihydrofusidic acid.

Example 16–19

16β-Thioethers of 16-deacetoxy-17(S),20(S)-dihydrofusidic Acid (Compound 116–119)

A. 16β-Thioethers of 3,11-bis-O-methoxymethyl-16-deacetoxy-17(S),20(S)-dihydrofusidic acid tert-butyl esters.

By following the procedure given in Example 15A and substituting the mercaptans listed in Table 5 for the isopropyl mercaptane, the 16β-thioethers of 3,11-bis-O-methoxymethyl-16-deacetoxy-17(S),20(S)-dihydrofusidic acid tert-butyl ester indicated in Table 5 were prepared.

TABLE 5

X

| Example | Mercaptan | Resulting compound R |
|---------|-----------|----------------------|
| 16A | ethyl mercaptan | CH₂CH₃ |
| 17A | 2,2,2-trichloroethyl mercaptan | CH₂CCl₃ |
| 18A | tert-butyl mercaptan | C(CH₃)₃ |
| 19A | methoxymethyl mercaptan | CH₂OCH₃ |

B. 16β-Thioethers of 16-deacetoxy-17(S),20(S)-dihydrofusidic acid

By following the procedure of Example 15B and substituting the 16β-thioethers of 3,11-bis-O-methoxymethyl-16-deacetoxy-17(S),20(S)-dihydrofusidic acid tert-butyl ester listed in Table 5 for the 3,11-bis-methoxymethyl-16-deacetoxy-16β-isopropylthio-17(S),20(S)-dihydrofusidic acid tert-butyl ester, the 16-deacetoxy-16β-alkylthio-17(S),20(S)-dihydrofusidic acids listed in Table 6 were obtained.

TABLE 6

XI

| Example | Resulting compound No | R |
|---------|----------------------|---|
| 16B | 116 | CH₂CH₃ |
| 17B | 117 | CH₂CCl₃ |
| 18B | 118 | C(CH₃)₃ |
| 19B | 119 | CH₂OCH₃ |

Example 20

16-Deacetoxy-16β-isopropylthio-17(S),20(S);24,25-tetrahydrofusidic Acid (Compound 120)

By following the procedure of Example 2 and replacing the 17(S),20(S)-dihydrofusidic acid with 16-deacetoxy-16β- isopropylthio-17(S),20(S)-dihydrofusidic acid, 16-deacetoxy-16β-isopropylthio-17(S),20(S),24,25-tetrahydrofusidic acid was prepared.

Example 21

16-Deacetoxy-16β-acetylthio-17(S),20(S)-dihydrofusidic Acid (Compound 121)

A. 3,11-Bis-O-methoxymethyl-16-deacetyl-16β-acetylthio-17(S),20(S)-dihydrofusidic acid tert-butyl ester To a solution of 3,11-bis-O-methoxymethyl-16-deacetoxy-16α-bromo-17(S),20(S)-dihydrofusidic acid tert-butyl ester (19), (700 mg, 1 mmol) in dimethylformamide (6 ml) was added solid potassium thioacetate (228 mg, 2 mmol) and the reaction mixture was stirred at room temperature for 20 hours. After this time the reaction mixture was diluted with diethyl ether (50 ml), transferred to a separatory funnel and washed twice with water (2×10 ml) and brine (10 ml). The organic layer was dried over anhydrous sodium sulphate and concentrated in vacuo to yield 3,11-bis-O-methoxymethyl-16-deacetyl-16β-acetylthio-17(S),20(S)-dihydrofusidic acid tert-butyl ester.

B. 16-Deacetoxy-16β-acetylthio-17(S),20(S)-dihydrofusidic acid

To a solution of the tert-butyl ester from A in tetrahydrofuran (5 ml) was added 2N aqueous hydrochloric acid (5 ml) and was vigorously stirred at 60° C. for four hours. The reaction mixture was allowed to attain room temperature, diluted with ethyl acetate (25 ml) and transferred to a separatory funnel. The two layers were separated and the organic layer was washed twice with water (2×5 ml) and twice with brine (2×5 ml). The organic layer was dried over sodium sulphate and concentrated in vacuo to yield 16-deacetoxy-16β- acetylthio-17(S),20(S)-dihydrofusidic acid as a colourless foam.

Example 22

16-Deactoxy-16β-benzoylthio-17(S),20(S)-dihydrofusidic Acid (Compound 122)

A. 3,11-Bis-O-methoxymethyl-16-deacetoxy-16β-benzoylthio-17(S),20(S)-dihydrofusidic acid tert-butyl ester By following the procedure in Example 17A but substituting the potassium thioacetate with potassium thiobenzoate, 3,11-bis-O-methoxymethyl-16-deacetoxy-16β-benzoylthio-17(S),20(S)-dihydrofusidic acid tert-butyl ester was obtained.

B. 16-Deacetoxy-16β-benzoylthio-17(S),20(S)-dihydrofusidic acid

By following the procedure in Example 17B but substituting the 3,11-bis-O-methoxymethyl-16-deacetoxy-16β-acetylthio-17(S),20(S)-dihydrofusidic acid tert-butyl ester with 3,11-bis-O-methoxymethyl-16-deacetoxy-16β-benzoylthio-17(S),20(S)-dihydrofusidic acid tert-butyl ester, 16-deacetoxy-16β-benzoylthio-17(S),20(S)-dihydrofusidic acid was obtained.

Example 23

16-Deacetoxy-16β-ethoxy-17(S),20(S)-dihydrofusidic Acid (Compound 123)

Silver carbonate (550 mg, 2 mmol) was added to a suspension of 3,11-O-bis-methoxymethyl-16-deacetoxy-16α-bromo-17(S),20(S)-dihydrofusidic acid phenacyl ester (750 mg, 1 mmol) in ethanol (10 ml), and, after being protected from light, the reaction mixture was stirred at room temperature for 18 hours. Insoluble material was filtered off and washed twice with ethanol (2×2 ml). To the combined filtrate and washings was added 5 N aqueous sodium hydroxide (4 ml), and the mixture was refluxed for 2 hours. The reaction mixture was allowed to attain room temperature and was acidified with 4 N hydrochloric acid. The major part of ethanol was removed in vacuo and to the residue was added ethyl acetate (50 ml) and water (20 ml). The two layers were stirred vigorously for 30 min, transferred to a separatory funnel and separated. The aqueous layer was extracted with ethyl acetate (50 ml). The combined organic extracts were washed with water (20 ml) and brine (20 ml), dried over anhydrous sodium sulphate and concentrated in vacuo to yield an oily residue. The crude product was dissolved in anhydrous dichloromethane under argon and cooled at 0° C. To the cooled mixture was added 4 Å molecular sieves (1 g) and trimethyl bromosilane (1.1 ml, 8.8 mmol), and the resulting mixture was stirred for 5 hours. After this time the reaction mixture was diluted with ethyl acetate (50 ml) and water (20 ml) and transferred to a separatory funnel. The two layers were shaken and separated. The aqueous layer was extracted with ethyl acetate (50 ml) and the combined organic extracts were washed with brine (30 ml), dried over anhydrous sodium sulphate and concentrated in vacuo to yield 16-deacetoxy-16β-ethoxy-17(S),20(S)-dihydrofusidic acid.

$^{13}$C NMR, (CD$_3$OD): 181.2, 132.8, 125.1, 82.9, 72.5, 69.4, 66.4, 50.8, 47.5, 46.6, 41.9, 39.3, 39.1, 38.2, 37.9, 37.1, 36.1, 34.4, 33.1, 31.1, 26.5, 25.9, 23.8, 23.6, 22.7, 17.8, 17.3, 16.5, 15.2

Example 24–29

16-Deacetoxy-16β-alkyloxy-17(S),20(S)-dihydrofusidic Acids (Compounds 124–129)

By substituting ethanol in the procedure of Example 21 with the alcohols listed in Table 6, the 16-deacetoxy-16β-alkyloxy-17(S),20(S)-dihydrofusidic acids listed in Table 7 were obtained.

TABLE 7

XII

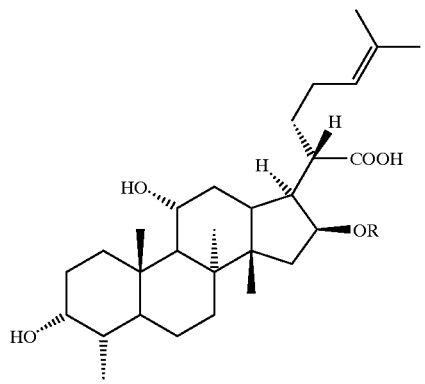

| | | Resulting compound | |
|---|---|---|---|
| Example | Alcohol | No. | R |
| 24 | 2,2,2-Trifluoroethanol | 124 | CH$_2$CF$_3$ |
| 25 | Propanol | 125 | CH$_2$CH$_2$CH$_3$ |
| 26 | Isopropanol | 126 | CH(CH$_3$)$_2$ |
| 27 | 1,3-Difluoroisopropanol | 127 | CH(CH$_2$F)$_2$ |
| 28 | Methoxymethanol | 128 | CH$_2$OCH$_3$ |
| 29 | 2,2,2-Trichloroethanol | 129 | CH$_2$CCl$_3$ |

Compound 126, $^{13}$(CD$_3$OD): 181.1, 132.9, 125.0, 99.3, 83.6, 72.5, 69.4, 56.3, 50.9, 50.6, 3, 38.2, 37.9, 37.0, 36.2, 34.2, 33.1, 31.1, 26.5, 25.9, 23.8, 23.5, 22.7, 17.8, 17.3, 16.5

Example 30

16-Deacetoxy-16β-(2'-azidoethoxy)-17(S),20(S)-dihydrofusidic Acid (Compound 130)

A. 3,11-Bis-O-methoxymethyl-16-deacetoxy-16β-(2'-hydroxyethoxy)-17(S),20(S)-dihydrofusidic acid tert-butyl ester To a solution of 3,11-bis-O-methoxymethyl-16-deacetoxy-16α-bromo-17(S),20(S)-dihydrofusidic acid tert-butyl ester (19), (1400 mg, 2 mmol) in a 1:1 mixture of ethylene glycol mono- and diacetate (8 ml) was added silver carbonate (1.1 g, 4 mmol). After being protected from light, the mixture was stirred for three days at room temperature. After removal of solvents under reduced pressure, the liquid residue was diluted with methanol (40 ml), potassium carbonate was added and the mixture was stirred for 30 min at room temperature. The mixture was concentrated in vacuo, and the resulting oily residue was dissolved in diethyl ether (40 ml) and water (40 ml) and neutralised with diluted hydrochloric acid. The two layers were separated and the aqueous layer was re-extracted with diethyl ether (20 ml). The combined organic layers were washed with water (20 ml) and brine (20 ml), dried over anhydrous sodium sulphate and concentrated in vacuo. The crude product was purified by column chromatography using ethyl acetate and low boiling petroleum ether as eluant yielding 3,11-bis-O-methoxymethyl-16-deacetoxy-16β-(2'-hydroxyethoxy)-17(S),20(S)-dihydrofusidic acid tert-butyl ester.

B. 3,11-Bis-O-methoxymethyl-16-deacetoxy-16β-(2'-bromoethoxy)-17(S),20(S)-dihydrofusidic acid tert-butyl ester.

Phenyl N,N-dimethylformimidate bromide (740 mg, 3.2 mmol) was added to a solution of 3,11-bis-O-methoxymethyl-16-deacetoxy-16β-(2'-hydroxyethoxy)-17(S),20(S)-dihydrofusidic acid tert-butyl ester from A (670 mg), and the resulting mixture was stirred for 16 hours at room temperature. After dilution with diethyl ether (30 ml), the mixture was transferred to a separatory funnel and washed thrice with water (3×10 ml) and brine (10 ml), and the organic layer was dried over anhydrous sodium sulphate and concentrated in vacuo. The pale red residue was purified by column chromatography using ethyl acetate and low boiling petroleum ether as eluant yielding 3,11-bis-O-methoxymethyl-16-deacetoxy-16β-(2'-bromoethoxy)-17(S),20(S)-dihydrofusidic acid tert-butyl ester.

C. 3,11-Bis-O-methoxymethyl-16-deacetoxy-16β-(2'-azidoethoxy)-17(S),20(S)-dihydrofusidic acid tert-butyl ester A solution of 3,11-bis-O-methoxymethyl-16-deacetoxy-16β-(2'-bromoethoxy)-17(S),20(S)-dihydrofusidic acid tert-butyl ester from B (370 mg, 0.5 mmol) and lithium azide (125 mg, 2.5 mmol) in dimethylformamide (8 ml) was stirred for 18 hours at room temperature. The solution was thereafter diluted with diethyl ether (40 ml), washed thrice with water (3×10 ml) and brine (10 ml). The organic layer was dried over anhydrous sodium sulphate and concentrated in vacuo to yield 3,11-bis-O-methoxymethyl-16-deacetoxy-16β-(2'-azidoethoxy)-17(S),20(S)-dihydrofusidic acid tert-butyl ester.

D. 16-Deacetoxy-16β-(2'-azidoethoxy)-17(S),20(S)-dihydrofusidic acid

A solution of 3,11-bis-O-methoxymethyl-16-deacetoxy-16β-(2'-azidoethoxy)-17(S),20(S)-dihydrofusidic acid tert-butyl ester (300 mg, 0.4 mmol) in tetrahydrofuran (5 ml) was added 2N aqueous hydrochloric acid (5 ml) and heated at 60° C. for four hours. The reaction mixture was allowed to attain room temperature, diluted with ethyl acetate (25 ml) and transferred to a separatory funnel. The two layers were separated and the organic layer was washed twice with water (2×5 ml) and twice with brine (2×5 ml). The organic layer was dried over sodium sulphate and concentrated in vacuo to yield 16-deacetoxy-16β-(2'-azidoethoxy)-17(S),20(S)-dihydrofusidic acid.

Example 31

16-Deacetoxy-16β-(2'-hydroxyethoxy)-17(S),20(S)-dihydrofusidic Acid (Compound 131)

By following the procedure of example 30D substituting 3,11-bis-O-methoxymethyl-16-deacetoxy-16β-(2'-azidoethoxy)-17(S),20(S)-dihydrofusidic acid tert-butyl ester with 3,11-bis-O-methoxymethyl-16-deacetoxy-16β-(2'-hydroxyethoxy)-17(S),20(S)-dihydrofusidic acid tert-butyl ester from Example 30A, 16-deacetoxy-16β-(2'-hydroxyethoxy)-17(S),20(S)-dihydrofusidic acid was obtained.

Example 32

17(S),20(S)-Dihydrofusidic Acid Sodium Salt

17(S),20(S)-Dihydrofusidic acid (400 mg, 0.77 mmol) was dissolved in methanol (0.4 ml) and acetone (1.2 ml) and neutralised with 4N sodium hydroxide. Diethyl ether was added slowly until precipitation of colourless crystals. 350 mg of colourless crystals were collected by filtration and dried in the air.

$^{13}$C NMR, (CD$_3$OD), 173.1, 131.8, 126.2, 78.3, 72.6, 69.4, 50.8, 50.6, 46.6, 41.9, 41.8, 39.6, 38.2, 38.0, 37.1, 36.2, 35.2, 33.1, 31.1, 27.2, 25.9, 23.7, 23.6, 22.6, 21.2, 17.9, 16.5

Example 33

17(S),20(S)-Dihydrofusidic Acid Diethanolamine Salt

17(S),20(S)-Dihydrofusidic acid (450 mg, 0.87 mmol) was dissolved in acetone (1 ml) and diethanolamine (0.1 ml, 1 mmol) and stored at room temperature for 24 hours. After this time diethyl ether was added slowly and the resulting solution was stored at 2° C. for several days yielding 380 mg semi-crystalline compound.

Example 34

Cream

| | |
|---|---|
| 16-Deacetoxy-16β-ethoxy-17(S),20(S)-dihydrofusidic acid sodium salt | 1 g |
| Petrolatum | 7.5 g |
| Liquid paraffin | 7.5 g |
| Spermaceti | 2.5 g |
| Sorbitane monopalmitate | 2.5 g |
| Polyoxyethylene sorbitane monopalmitate | 2.5 g |
| Water | 26.5 g |
| | 50 g |

Heat petrolatum, paraffin, spermaceti, sorbitane monopalmitate and polyoxyethylene sorbitane monopalmitate to 70° C. and slowly add water under continuous stirring. Continue stirring until the cream has cooled. Triturate 16-deacetoxy-16β-ethoxy-17(S),20(S)-dihydrofusidic acid sodium salt into the cream base and homogenise using a roller mill. Fill the cream into aluminium collapsible tubes.

Example 35

Ointment

| | |
|---|---|
| 16-Deacetoxy-16β-ethoxy-17(S),20(S)-dihydrofisidic acid sodium salt | 1 g |
| Liquid paraffin | 6.9 g |
| Cetanol | 0.2 g |
| Lanolin anhydrous | 2.3 g |
| Petrolatum | 39.6 g |
| | 50 g |

Melt paraffin, cetanol, lanolin and petrolatum at 70° C. After cooling to below 40° C. triturate 16-deacetoxy-16β-ethoxy-17(S),20(S)-dihydrofusidic acid sodium salt. Fill the ointment into lacquered collapsible aluminium tubes.

Example 36

Capsule

| | |
|---|---|
| 16-Deacetoxy-16β-acetylthio-17(S),20(S)-dihydrofusidic acid sodium salt | 25 g |
| Microcrystalline cellulose | 14.5 g |
| Magnesium stearate | 0.5 g |
| | 40 g |

Pass the ingredients through a 60 mesh sieve and mix for 10 min. Fill the mixture into hard gelatine capsules using a capsule fill weight of 400 mg.

Example 37

Tablets

| | |
|---|---|
| 16-Deacetoxy-16β-(2',2',2'-trifluoroethoxy)-17(S),20(S)-dihydro-fusidic acid sodium salt | 25 g |
| Avicel ™ | 12 g |
| STA-Rx 1500 | 12 g |
| Magnesium stearate | 1 g |
| | 50 g |

16-Deacetoxy-16β-(2',2',2'-trifluoroethoxy)-17(S),20(S)-dihydrofusidic acid sodium salt, Avicel™ and STA-Rx are mixed together, sieved through a 0.7 mm sieve and thereafter mixed with magnesium stearate: The mixture is pressed into tablets each of 500 mg.

Example 38

Suspension

| | |
|---|---|
| 16-Deacetoxy-16β-acetylthio-17(S),20(S)-dihydrofusidic acid sodium salt | 1 g |
| Citric acid | 0.09 g |
| Sodium monohydrogenphosphate | 0.14 g |
| Sucrose | 5 g |
| Tween ™ 80 | 0.01 g |
| Potassium sorbate | 0.04 g |

-continued

| | |
|---|---|
| Carboxymethylcellulose-Na | 0.1 g |
| Water | qs. to 100 ml suspension. |

The crystals are micronized and suspended in a solution of citric acid, sodium monohydrogen phosphate, sucrose, potassium sorbate and Tween™ 80 in 10 ml water, if necessary with slight warming. Carboxymethylcellulose-Na is dissolved in 4 ml boiling water. After cooling, it is added to the other ingredients. The suspension is homogenised in a blender and finally water is added to a total volume of 100 ml.

Example 39

Ointment

| | |
|---|---|
| A: 16-Deacetoxy-16β-(2',2',2'-trifluoroethoxy)-17(S),20(S)-dihydrofusidic acid sodium salt | 1 g |
| B: One of the compounds: hydrocortisone, triamcinolone or fluocinolone | 0.5 g |
| Liquid paraffin | 6.9 g |
| Cetanol | 0.2 g |
| Lanolin anhydrous | 2.3 g |
| Petrolatum | 39.1 g |
| | 50 g |

Melt paraffin, cetanol, lanolin and petrolatum at 70° C. After cooling to below 40° C., triturate A and B. Fill the ointment into lacquered collapsible aluminium tubes.

Example 40

Ointment

| | |
|---|---|
| A: 16-Deacetoxy-16β-(2',2',2'-trifluoroethoxy)-17(S),20(S)-dihydrofusidic acid sodium salt | 1.5 g |
| B: Tetracycline | 1.5 g |
| Liquid paraffin | 13.8 g |
| Cetanol | 0.4 g |
| Lanolin anhydrous | 4.6 g |
| Petrolatum | 78.2 g |
| | 100 g |

Melt paraffin, cetanol, lanolin and petrolatum at 70° C. After cooling to below 40° C., triturate A and B. Fill the ointment into lacquered collapsible aluminium tubes.

Example 41

Eye Gel

| | |
|---|---|
| 17(S),20(S)-Dihydrofusidic acid | 10 g |
| Benzalkonium chloride | 0.1 g |
| Carbomer | 5 g |
| Mannitol | 50 g |
| Sodium edetate | 0.5 g |
| Sodium hydroxide | q.s. |
| Sterile water | up to 100 g |

Dissolve disodium edetate and mannitol in water for injection in a stainless steel vessel equipped with a stirring tool and a built-in homogenizer. Add Carbomer 934P, evacuate the vessel and autoclave the dispersion under slow stirring and homogenizing at high speed. Cool down to 70° C., stop agitator and homogenizer. Add 17(S),20(S)-dihydrofusidic acid micronized, sterile—evacuate the vessel and let the 17(S),20(S)-dihydrofusidic acid sink during slow agitation. Homogenize at high speed for 10 minutes at 70° C. Cool down below 30° C. during stirring and homogenizing at low speed. Add a sterile solution of benzalkonium chloride in water for injection under slow stirring. Neutralise the carbomer 934 P by adding a sterile solution of sodium hydroxide 1.050 kg in water for injection. Stir and homogenize at low speed for 5 minutes. Adjust—if necessary—the pH to 5.4–5.8. Transfer the eye gel to storage tanks using nitrogen pressure and the low speed homogenizing transfer system. Store at room temperature until filling. The eye gel is filled aseptically in sterile tubes using a fill weight of 3.5 g.

What is claimed is:

1. A compound of the formula Ia:

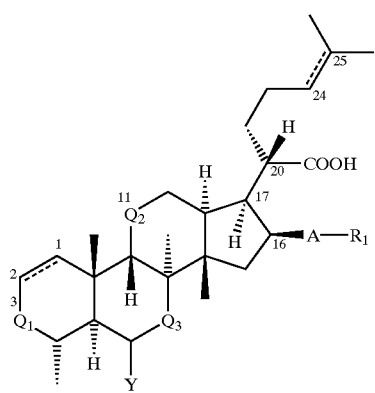

wherein $Q_1$, $Q_2$ and $Q_3$ are the same or different and independently represent a —(CO)— group; a —(CHOH)— group; a —(CHOR)— group; a —(CASH)— group; a —(NH)— group; a —(CHNH$_2$)— group; or a —(CHNHR)— group, wherein R represents an alkyl radical having 1 to 4 carbon atoms or an acyl radical having 1 to 4 carbon atoms;

and wherein $Q_2$ and $Q_3$ may also independently represent a —(CH$_2$)— group;

Y represents hydrogen, hydroxy, an alkyl radical having 1 to 4 carbon atoms, or an acyl radical having 1 to 4 carbon atoms; A represents an oxygen or sulphur atom;

$R_1$ represents an alkyl radical having 1 to 4 carbon atoms, an olefinic group having 2 to 4 carbon atoms, a ($C_1$–$C_6$) acyl group, a ($C_3$–$C_7$)cycloalkylcarbonyl group or a benzoyl group, $R_1$ optionally being substituted with one or more halogen atoms and/or hydroxy, alkoxy or azido groups;

and pharmaceutically acceptable salts and easily hydrolysable esters thereof.

2. A compound of the formula I

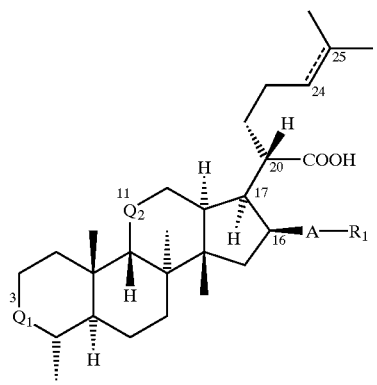

wherein $Q_1$ and $Q_2$ are the same or different and both represent a —(CHOH)— group; a —(CO)— group; or a —(CHSH)— group;

A represents an oxygen or a sulphur atom;

$R_1$ represents an alkyl radical having 1 to 4 carbon atoms, an olefinic group having 2 to 4 carbon atoms, a ($C_1$–$C_6$) acyl group, ($C_1$–$C_7$)cycloalkylcarbonyl group or a benzoyl group, $R_1$ optionally being substituted with one or more halogen atoms and/or hydroxy, alkoxy or azido groups; and pharmaceutically acceptable salts and easily hydrolysable esters thereof.

3. A compound according to claim 1 or 2 wherein $Q_1$ and $Q_2$ both represent a

group.

4. A compound according to claim 3 wherein the stereochemistry, when $Q_1$ and $Q_2$ refer to the

group, of the carbon atoms C-3 and C-11 is 3α-OH and 11α-OH, respectively, and the C-16 atom carrying the A group has the configuration —(S) denoted 16β.

5. A compound according to claims 1 or 2 wherein one of $Q_1$ or $Q_2$ represents —(CO)—.

6. A compound according to claims 1 or 2 wherein A represents oxygen.

7. A compound according to claims 1 or 2 wherein $R_1$ represents a ($C_1$–$C_4$)alkyl group, optionally substituted with one or more substituents selected from the group consisting of azido, hydroxy, and halogen selected from fluoro, chloro and bromo.

8. A compound according to claim 7 wherein $R_1$ represents a ($C_1$–$C_4$)alkyl group substituted with one or more halogen groups selected from fluoro and chloro.

9. A compound according to claims 1 or 2 wherein $R_1$ is selected from the group consisting of ethyl, 2,2,2-trifluoroethyl, 2,2,2-trichloroethyl, 2-azidoethyl, 2-hydroxyethyl, propyl and isopropyl, 1,3-difluoro-isopropyl, tert-butyl, acetyl, propionyl, chloroacetyl and trifluoroacetyl.

10. A compound according to claims 1 or 2 wherein $R_1$ is selected from the group consisting of ethyl, 2,2,2-trichloroethyl, 2-azidoethyl, isopropyl, tert-butyl and acetyl.

11. A compound according to claims 1 or 2 wherein the bond between C-24 and C-25 is a double bond.

12. A compound selected from the group consisting of
17(S),20(S)-Dihydrofusidic acid,
17(S),20(S),24,25-Tetrahydrofusidic acid,
11-Dehydro-17(S),20(S)-dihydrofusidic acid,
3-Dehydro-17(S),20(S)-dihydrofusidic acid,
16-Deacetoxy-16β-propionyloxy-17(S),20(S)-dihydrofusidic acid,
16-Deacetoxy-16β-(3'-chloropropionyloxy)-17(S),20(S)-dihydrofusidic acid,
16-Deacetoxy-16β-(2'-methylpropionyloxy)-17(S),20(S)-dihydrofusidic acid,
16-Deacetoxy-16β-cyclopropylcarbonyloxy-17(S),20(S)-dihydrofusidic acid,
16-Deacetoxy-16β-chloroacetoxy-17(S),20(S)-dihydrofusidic acid,
16-Deacetoxy-16β-bromoacetoxy-17(S),20(S)-dihydrofusidic acid,
16-Deacetoxy-16β-benzoyloxy-17(S),20(S)-dihydrofusidic acid,
16-Deacetoxy-16β-(4'-fluorobenzoyloxy)-17(S),20(S)-dihydrofusidic acid,
16-Deacetoxy-16β-cyclohexylcarbonyloxy-17(S),20(S)-dihydrofusidic acid,
16-Deacetoxy-16β-acryloyloxy-17(S),20(S)-dihydrofusidic acid,
16-Deacetoxy-16β-isopropylthio-17(S),20(S)-dihydrofusidic acid,
16-Deacetoxy-16β-ethylthio-17(S),20(S)-dihydrofusidic acid,
16-Deacetoxy-16β-(2',2',2'-trichloroethylthio)-17(S),20(S)-dihydrofusidic acid,
16-Deacetoxy-16β-tert-butylthio-17(S),20(S)-dihydrofusidic acid,
16-Deacetoxy-16β-methoxymethylthio-17(S),20(S)-dihydrofusidic acid,
16-Deacetoxy-16β-isopropylthio-17(S),20(S);24,25-tetrahydrofusidic acid,
16-Deacetoxy-16β-acetylthio-17(S),20(S)-dihydrofusidic acid,
16-Deacetoxy-16β-benzoylthio-17(S),20(S)-dihydrofusidic acid,
16-Deacetoxy-16β-ethoxy-17(S),20(S)-dihydrofusidic acid,
16-Deacetoxy-16β-(2',2',2'-trifluoroethoxy)-17(S),20(S)-dihydrofusidic acid,
16-Deacetoxy-16β-propoxy-17(S),20(S)-dihydrofusidic acid,
16-Deacetoxy-16β-isopropoxy-17(S),20(S)-dihydrofusidic acid,
16-Deacetoxy-16β-(1',3'-difluoroisopropoxy)-17(S),20(S)-dihydrofusidic acid,
16-Deacetoxy-16β-methoxymethoxy-17(S),20(S)-dihydrofusidic acid,
16-Deacetoxy-16β-(2',2',2'-trichloroethoxy)-17(S),20(S)-dihydrofusidic acid,
16-Deacetoxy-16β-(2'-azidoethoxy)-17(S),20(S)-dihydrofusidic acid,
16-Deacetoxy-16β-(2'-hydroxyethoxy)-17(S),20(S)-dihydrofusidic acid,
and pharmaceutically acceptable salts and easily hydrolysable esters thereof.

13. A compound according to claim 12 selected from the group consisting of 17(S),20(S)-Dihydrofusidic acid sodium salt and 17(S),20(S)-Dihydrofusidic acid diethanolamine salt.

14. A stereoisomer of a compound of claim 1 or 2 in pure form; or a mixture of such stereoisomers.

15. A pharmaceutical composition comprising a compound of claims 1 or 2 with a pharmaceutically acceptable, non-toxic carrier and/or auxiliary agent and optionally together with one or more other therapeutically active components.

16. A pharmaceutical composition comprising 17(S),20(S)-dihydrofusidic acid with a pharmaceutically acceptable, non-toxic carrier and/or auxiliary agent and optionally together with one or more other therapeutically active components.

17. A pharmaceutical composition according to claim 15 or 16 in a topical preparation form.

18. A pharmaceutical composition according to claim 17, where the topical preparation is an ointment.

19. A method of treating a patient in need of antimicrobial treatment, comprising administering to said patient an effective amount of the pharmaceutical composition of claim 15, optionally together or concomitantly with one or more other therapeutically active components.

* * * * *